(12) United States Patent
Chandra et al.

(10) Patent No.: US 9,120,893 B1
(45) Date of Patent: Sep. 1, 2015

(54) ALKOXY POLYCARBONATES, BISPHENOL MONOMERS AND METHODS OF MAKING AND USING THE SAME

(71) Applicant: SABIC Global Technologies B.V., Bergen op Zoom (NL)

(72) Inventors: Girish Chandra, Karnataka (IN); Edward J. Nesakumar, Karnataka (IN); Venkata Ramanarayanan Ganapathy Bhotla, Karnataka (IN); Sharankumar G. Shetty, Bangalore (IN); James Mahood, Evansville, IN (US); Robert R. Gallucci, Mt. Vernon, IN (US); Jan Henk Kamps, Bergen op Zoom (NL); Minor Senthil Kumar, Karnataka (IN)

(73) Assignee: SABIC Global Technologies B.V., Bergen op Zoom (NL)

( * ) Notice: Subject to any disclaimer, the term of this patent is extended or adjusted under 35 U.S.C. 154(b) by 0 days.

(21) Appl. No.: 14/265,237

(22) Filed: Apr. 29, 2014

(51) Int. Cl.
  *C08G 64/06* (2006.01)
  *C08G 64/24* (2006.01)
  *C08K 5/526* (2006.01)
  *C08L 69/00* (2006.01)
  *C07C 41/01* (2006.01)
  *C08G 64/14* (2006.01)

(52) U.S. Cl.
  CPC ............... *C08G 64/24* (2013.01); *C07C 41/01* (2013.01); *C08K 5/526* (2013.01); *C08L 69/00* (2013.01)

(58) Field of Classification Search
  USPC ......................................................... 528/204
  See application file for complete search history.

(56) References Cited

U.S. PATENT DOCUMENTS

| | | | |
|---|---|---|---|
| 3,635,895 | A | 1/1972 | Kramer et al. |
| 4,001,184 | A | 1/1977 | Scott |

*Primary Examiner* — Terressa Boykin
(74) *Attorney, Agent, or Firm* — Baker & Hostetler LLP

(57) ABSTRACT

Disclosed herein are alkoxy polycarbonates, ortho alkoxy bisphenol monomers, polymer compositions comprising ortho alkoxy bisphenol monomers, methods of preparing the ortho alkoxy bisphenol monomers, polymer compositions and articles made thereof. This abstract is intended as a scanning tool for purposes of searching in the particular art and is not intended to be limiting of the present disclosure.

48 Claims, 5 Drawing Sheets

ALKOXY POLYCARBONATES, BISPHENOL MONOMERS AND METHODS OF MAKING AND USING THE SAME

BACKGROUND

Development of alternatives to existing polycarbonates, polyesters and polyestercarbonates that maintain properties (high transparency and good melt stability) of the corresponding polymers are of great interest in the plastics industry and for the manufacturing industry. To achieve this, a suitable monomer for polymerization reactions is necessary to produce a polymer with the necessary properties.

Further, monomers or oligomers used in making the polycarbonate materials may not proceed to completion in some instances, thus leading to the presence of unreacted residual monomers or oligomers in the polymeric material. Additionally, when subjected to certain conditions, the polymeric materials can undergo degradation reactions, such as hydrolytic or thermolytic degradation, resulting in the formation of hydrolysis and/or thermolysis degradants or reaction products. In some aspects, the resulting degradants can correspond chemically to the monomeric starting materials initially used to manufacture polymeric materials. The presence of residual monomers, either as residues of polymerization or through degradation by thermal or hydrolytic means, is an area of growing regulatory concern.

This concern has led to extensive research to find suitable alternative monomers for polycarbonate materials whose residual monomers or degradation products exhibit desirable characteristics. Desirable characteristics of such degradants include, among other, extremely low, or even no estradiol binding activity.

Accordingly, there is a need for polymeric materials which, if having or generating residual monomers, comprise such monomers that have very low, or non-detectable, biological activity, for instance having extremely low or no estradiol binding activity compared to estradiol in the estradiol related receptor (ERR).

SUMMARY

The present invention relates to alkoxy polycarbonates, ortho alkoxy bisphenol monomers and methods of making the same. The method for making the ortho alkoxy bisphenol monomers comprises: a) providing a phenol having at least one alkoxy substituent ortho to the hydroxyl group; b) providing a ketone; and reacting the phenol and ketone in the presence of a catalyst under conditions effective to provide a reaction product comprising an ortho alkoxy bisphenol monomer; wherein the ortho alkoxy bisphenol monomer does not exhibit a half maximal inhibitory concentration ($IC_{50}$) less than 0.00025M for alpha or beta in vitro estradiol receptors. The ortho alkoxy bisphenol monomers can be used in the production of polycarbonate polymer compositions exhibiting properties such as low cost, high transparency and good melt stability. The resulting polymer compositions can be used in the manufacture of articles requiring materials with low cost, high transparency and good melt stability. These polycarbonate polymers when exposed to hydrolysis or thermal degradation may generate phenolic species which show very low or non-detectable interaction with biological systems for instance estradiol receptors.

In another aspect, the invention relates to a method for preparing a bisphenol monomer, the method comprising: a) providing guaiacol; b) providing acetone; and c) reacting the guaiacol and acetone under conditions effective to provide a reaction product comprising 4,4'(2,2'-isopropylidene)-bis (ortho methoxy)phenol (PBMP); wherein the PBMP does not exhibit a half maximal inhibitory concentration ($IC_{50}$) less than 0.00025M for alpha or beta in vitro estradiol receptors.

In various further aspects, the invention relates to polycarbonate polymers comprising the disclosed ortho alkoxy bisphenol monomers. In one aspect, the invention provides a polycarbonate comprising: a) repeating carbonate units derived from at least one ortho alkoxy bisphenol monomer; wherein the ortho alkoxy bisphenol monomer does not exhibit a half maximal inhibitory concentration ($IC_{50}$) less than 0.00025M for alpha or beta in vitro estradiol receptors; and wherein when the polycarbonate is subjected to conditions effective to provide at least one hydrolysis product, the at least one hydrolysis product does not exhibit a half maximal inhibitory concentration ($IC_{50}$) less than 0.00025M for alpha or beta in vitro estradiol receptors.

In various further aspects, the invention relates to a method for preparing a polycarbonate, the method comprising: a) providing a disclosed alkoxy bisphenol monomer; b) providing a carbonyl source reactant; and c) reacting the bisphenol monomer and carbonyl source reactant with a catalyst under conditions effective to provide a polycondensation reaction product comprising a polycarbonate; wherein when the polycarbonate provided in step c) is subjected to conditions effective to provide at least one hydrolysis product, each of the at least one hydrolysis products does not exhibit a half maximal inhibitory concentration ($IC_{50}$) less than 0.00025M for alpha or beta in vitro estradiol receptors.

In various further aspects, the invention relates to articles comprising the disclosed compositions.

In a further aspect, the invention relates to methods of making the disclosed compositions.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Additional aspects of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE FIGURES

The accompanying figures, which are incorporated in and constitute a part of this specification, illustrate several aspects and together with the description serve to explain the principles of the invention.

DETAILED DESCRIPTION OF THE INVENTION

Figure 1:
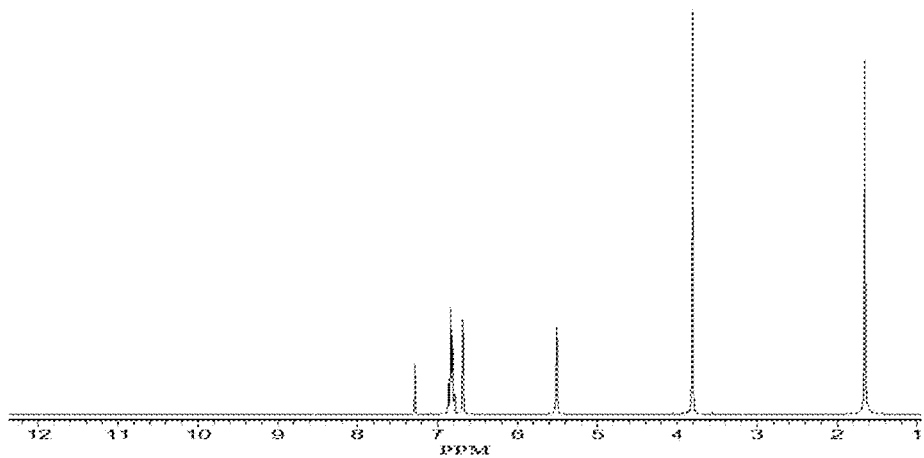
FIG. 1 shows a representative $^1$H NMR of PBMP monomer prepared according to the present invention.

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such can, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of aspects described in the specification.

All publications mentioned herein are incorporated herein by reference to disclose and describe the methods and/or materials in connection with which the publications are cited.

A. DEFINITIONS

It is also to be understood that the terminology used herein is for the purpose of describing particular aspects only and is not intended to be limiting. As used in the specification and in the claims, the term "comprising" can include the aspects "consisting of" and "consisting essentially of." Unless defined otherwise, all technical and scientific terms used herein have the same meaning as commonly understood by one of ordinary skill in the art to which this invention belongs. In this specification and in the claims which follow, reference will be made to a number of terms which shall be defined herein.

As used in the specification and the appended claims, the singular forms "a," "an" and "the" include plural referents unless the context clearly dictates otherwise. Thus, for example, reference to "a polycarbonate polymer" includes mixtures of two or more polycarbonate polymers.

As used herein, the term "combination" is inclusive of blends, mixtures, alloys, reaction products, and the like.

Ranges can be expressed herein as from one particular value, and/or to another particular value. When such a range is expressed, another aspect includes from the one particular value and/or to the other particular value. Similarly, when values are expressed as approximations, by use of the antecedent 'about,' it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "about" and "at or about" mean that the amount or value in question can be the value designated some other value approximately or about the same. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

As used herein, the terms "optional" or "optionally" means that the subsequently described event or circumstance can or cannot occur, and that the description includes instances where said event or circumstance occurs and instances where it does not. For example, the phrase "optionally substituted alkyl" means that the alkyl group can or cannot be substituted and that the description includes both substituted and unsubstituted alkyl groups.

As used herein, the term "effective amount" refers to an amount that is sufficient to achieve the desired modification of a physical property of the composition or material. For example, an "effective amount" of a filler refers to an amount that is sufficient to achieve the desired improvement in the property modulated by the formulation component, e.g. achieving the desired level of modulus. The specific level in terms of wt % in a composition required as an effective amount will depend upon a variety of factors including the amount and type of polycarbonate, amount and type of polycarbonate, amount and type of thermally conductive filler, and end use of the article made using the composition.

Disclosed are the components to be used to prepare the compositions of the invention as well as the compositions themselves to be used within the methods disclosed herein.

These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific aspect or combination of aspects of the methods of the invention.

References in the specification and concluding claims to parts by weight of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

As used herein the terms "weight percent," "wt %," and "wt. %," which can be used interchangeably, indicate the percent by weight of a given component based on the total weight of the composition, unless otherwise specified. That is, unless otherwise specified, all wt % values are based on the total weight of the composition. It should be understood that the sum of wt % values for all components in a disclosed composition or formulation are equal to 100.

Compounds are described using standard nomenclature. For example, any position not substituted by any indicated group is understood to have its valence filled by a bond as indicated, or a hydrogen atom. A dash ("-") that is not between two letters or symbols is used to indicate a point of attachment for a substituent. For example, —CHO is attached through carbon of the carbonyl group. Unless defined otherwise, technical and scientific terms used herein have the same meaning as is commonly understood by one of skill in the art to which this invention belongs.

The term "alkyl group" as used herein is a branched or unbranched saturated hydrocarbon group of 1 to 24 carbon atoms, such as methyl, ethyl, n propyl, isopropyl, n butyl, isobutyl, t butyl, pentyl, hexyl, heptyl, octyl, decyl, tetradecyl, hexadecyl, eicosyl, tetracosyl and the like. A "lower alkyl" group is an alkyl group containing from one to six carbon atoms.

The term "aryl group" as used herein is any carbon-based aromatic group including, but not limited to, benzene, naphthalene, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorus. The aryl group can be substituted or unsubstituted. The aryl group can be substituted with one or more groups including, but not limited to, alkyl, alkynyl, alkenyl, aryl, halide, nitro, amino, ester, ketone, aldehyde, hydroxy, carboxylic acid, or alkoxy.

The term "aralkyl" as used herein is an aryl group having an alkyl, alkynyl, or alkenyl group as defined above attached to the aromatic group. An example of an aralkyl group is a benzyl group.

The term "carbonate group" as used herein is represented by the formula OC(O)OR, where R can be hydrogen, an alkyl, alkenyl, alkynyl, aryl, aralkyl, cycloalkyl, halogenated alkyl, or heterocycloalkyl group described above.

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-dihydroxyphenyl radical in a particular compound has the structure:

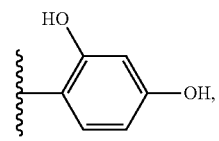

regardless of whether 2,4-dihydroxyphenyl is used to prepare the compound. In some aspects the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5,6,7,8-tetrahydro-2-naphthyl radical. In some aspects, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

As used herein, the terms "number average molecular weight" or "$M_n$" can be used interchangeably, and refer to the statistical average molecular weight of all the polymer chains in the sample and is defined by the formula:

$$M_n = \frac{\Sigma N_i M_i}{\Sigma N_i}, M_n = \frac{\Sigma N_i M_i}{\Sigma N_i}.$$

where $M_i$ is the molecular weight of a chain and $N_i$ is the number of chains of that molecular weight. $M_n$ can be determined for polymers, e.g., polycarbonate polymers, by methods well known to a person having ordinary skill in the art using molecular weight standards, e.g. polycarbonate standards or polystyrene standards, preferably certified or traceable molecular weight standards.

$$M_n = \frac{\Sigma N_i M_i}{\Sigma N_i},$$

As used herein, the terms "weight average molecular weight" or "Mw" can be used interchangeably, and are defined by the formula:

$$M_w = \frac{\Sigma N_i M_i^2}{\Sigma N_i M_i},$$

where $M_i$ is the molecular weight of a chain and $N_i$ is the number of chains of that molecular weight. Compared to $M_n$, $M_w$ takes into account the molecular weight of a given chain in determining contributions to the molecular weight average. Thus, the greater the molecular weight of a given chain, the more the chain contributes to the $M_w$. $M_w$ can be determined for polymers, e.g. polycarbonate polymers, by methods well known to a person having ordinary skill in the art using molecular weight standards, e.g. polycarbonate standards or polystyrene standards, preferably certified or traceable molecular weight standards.

As used herein, "polycarbonate" refers to an oligomer or polymer comprising residues of one or more dihydroxy compounds, e.g., dihydroxy aromatic compounds, joined by carbonate linkages; it also encompasses homopolycarbonates, copolycarbonates, and (co)polyester carbonates.

The terms "residues" and "structural units", used in reference to the constituents of the polymers, are synonymous throughout the specification.

As used herein the terms "weight percent," "wt %," and "wt. %," which can be used interchangeably, indicate the percent by weight of a given component based on the total weight of the composition, unless otherwise specified. That is, unless otherwise specified, all wt % values are based on the total weight of the composition. It should be understood that the sum of wt % values for all components in a disclosed composition or formulation are equal to 100.

As used herein, the terms "BisA," "BPA," or "bisphenol A," which can be used interchangeably, refers to a compound having a structure represented by the formula:

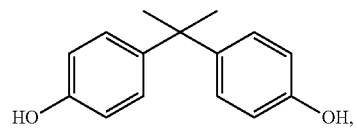

BisA can also be referred to by the name 4,4'-(propane-2,2-diyl)diphenol; p,p'-isopropylidene bisphenol; or 2,2-bis(4-hydroxyphenyl)propane. BisA has the CAS #80-05-7.

As used herein, the terms "PBMP," "G-BPA," "DMBPA," "guaiacol bisphenol A," or "dimethoxy bisphenol A," which can be used interchangeably, refers to a compound having a structure represented by the formula,

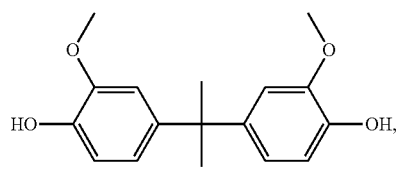 [SMILES: COc1cc(C(C)(C)c2ccc(O)c(OC)c2)ccc1O]

PBMP can also be referred to by the name 4,4'(2,2'-isoPropylidene)-Bis(ortho Methoxy) Phenol.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. ORTHO ALKOXY BISPHENOL MONOMER

In accordance with the purpose(s) of the invention, as embodied and broadly described herein, the invention, in one aspect, relates to ortho alkoxy bisphenol monomers useful in producing polymers, methods of making same, thermoplastic compositions comprising same, and articles comprising same.

In various aspects, the present invention relates to methods for preparing an alkoxy bisphenol monomer. In further aspects, the alkoxy bisphenol monomer is an ortho alkoxy bisphenol monomer. In still further aspects, the ortho alkoxy bisphenol monomer has a structure represented by a formula:

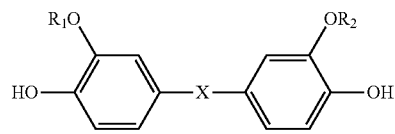

wherein each of $R^1$ and $R^2$ is independently selected from $C_1$-$C_{26}$ alkyl and $C_6$-$C_{26}$ alkaryl; and X is alkyl or arylalkyl. In yet further aspects, X is a bridging group connecting the two hydroxy-substituted aromatic groups, where the bridging group and the hydroxy substituent of each C6 arylene group are disposed meta, or para (specifically para) to each other on the C6 arylene group, for example, and without limitation, a single bond, —O—, —S—, —S(O)—, —S(O)$_2$—, —C(O)—, or a C$_3$-C$_{18}$ organic group, which can be cyclic or acyclic, aromatic or non-aromatic, and can further comprise heteroatoms such as halogens, oxygen, nitrogen, sulfur, silicon, or phosphorous. For example, according to still further aspects, X can be a substituted or unsubstituted C$_3$-C$_{12}$ cycloalkylidene; a C$_3$-C$_{12}$ alkylidene of the formula —C(R$^c$)(R$^d$)— wherein R$^c$ and R$^d$ are each independently hydrogen, C$_1$-C$_{12}$ alkyl, C1-C$_{12}$ cycloalkyl, C$_7$-C$_{12}$ arylalkyl. In yet further aspects, each of R$^1$ and R$^2$ is independently selected from methyl, ethyl, propyl, octyl, isooctyl, benzyl, ethyl phenyl, butyl phenyl, propyl diphenyl, and cyclohexyl phenyl. In even further aspects, each of R$^1$ and R$^2$ is methyl. In even further aspects, X is selected from methylene, cyclohexyl-methylene, 2-[2.2.1]-bicycloheptylidene, ethylidene, isopropylidene, neopentylidene, cyclohexylidene, cyclopentadecylidene, cyclododecylidene, and adamantylidene. In other aspects, X is selected from ethylidene, isopropylidene, isobutylidene neopentylidene, cyclohexylidene, alkyl substituted cyclohexylidene, aryl, cyclopentadecylidene, cyclododecylidene, sulfo, oxo, and bicycloheptylidene; and wherein each of R1 and R2 is independently selected from methyl, ethylidene, propylidene, butylidene, benzyl, phenyl, C1 to C4 alkyl phenyl, and cyclohexylidene.

In some aspects, the alkoxy bisphenol monomer is 4,4'(2, 2'-isoPropylidene)-Bis(ortho Methoxy)Phenol (PBMP), and has a structure represented by the formula:

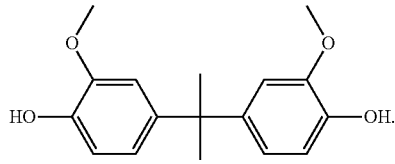 [SMILES: COc1cc(C(C)(C)c2ccc(O)c(OC)c2)ccc1O]

In one aspect, the present invention provides alkoxy bisphenol monomers that do not exhibit significant estradiol-like binding activity. In a further aspect, the lack of significant estradiol like binding activity of these bisphenol monomers can be characterized by a determination of their half maximal inhibitory concentration (IC$_{50}$) for alpha or beta in vitro estradiol receptors. For example, bisphenol monomers of the present invention do not exhibit a half maximal inhibitory concentration (IC$_{50}$) less than 0.00025M for alpha or beta in vitro estradiol receptors. In further aspects, bisphenol monomers of the present invention do not exhibit a half maximal inhibitory concentration (IC$_{50}$) less than 0.0003M, 0.00035M, 0.0004M, 0.00045M, 0.0005M, 0.00075M, or even 0.001M, for alpha or beta in vitro estradiol receptors. In still further aspects, bisphenol monomers of the present invention do not exhibit any identifiable half maximal inhibitory concentration (IC$_{50}$) greater than or equal to about 0.00025M, 0.0003M, 0.00035M, 0.0004M, 0.00045M, 0.0005M, 0.00075M, or even 0.001M, for alpha and/or beta in vitro estradiol receptors.

In some aspects, the disclosed monomer is a bio-based material. In further aspects, the monomer is derived from a biological material. In some aspects, the monomer is wholly derived from a biological material. In other aspects, the monomer is partly derived from a biological material. In further aspects, the monomer not derived from organic material that has been transformed by geological processes into petroleum, petrochemicals, and combinations thereof. In further aspects, the ortho alkoxy bisphenol monomer is from greater than 0 wt % to about 100 wt % derived from bio-based material, including exemplary wt % values of 1, 5, 10, 20, 30, 40, 50, 60, 70, 80, 90, and 99 wt. % derived from bio-based material. In still further aspects, the bio-based material comprises at least one lignocellulosic material, plant material, or a combination thereof. In even further aspects, bio-based material is a bio-based oil, pyrolysis oil, or lignin-rich waste from a biorefinery. In various aspects, a biological derived material, as described herein, can be determined by a carbon isotope ($^{13}$C3/$^{14}$C) ratio, for example, as per ASTM D6866-12 "Standard Test Methods for Determining the Biobased Content of Solid, Liquid, and Gaseous Samples Using Radiocarbon Analysis".

C. METHODS OF MAKING THE MONOMERS

In various aspects, the present invention provides a method for preparing an alkoxy bisphenol monomer, the method comprising: a) providing an alkoxy phenol; b) providing a ketone; and c) reacting the alkoxy phenol and ketone under conditions effective to provide a reaction product comprising an ortho alkoxy bisphenol monomer; wherein the an ortho alkoxy bisphenol monomer does not exhibit a half maximal inhibitory concentration (IC$_{50}$) less than 0.00025M for alpha or beta in vitro estradiol receptors.

In some aspects, the phenol comprises any phenol having at least one alkoxy substituent ortho to the hydroxyl group. In further aspects, the alkoxy group comprises —OR, wherein R is selected from C1-C26 alkyl and C6-C26 alkaryl. In still further aspects, R is selected from methyl, ethyl, propyl, octyl, isooctyl, benzyl, ethyl phenyl, butyl phenyl, propyl diphenyl, and cyclohexyl phenyl. In even further aspects, R is methyl.

In some aspects, the phenol is guaiacol (2-methoxyphenol). In still further aspects, the phenol comprises at least about 20 wt % guaiacol. In yet further aspects, the phenol comprises from greater than 0 wt % guaiacol to about 100 wt % guaiacol, including exemplary wt % of 1, 5, 10, 20, 30, 40, 50, 60, 70, 80, and 90 wt %.

In some aspects, the alkoxy phenol is a bio-based material. In further aspects, the alkoxy phenol derived from a biological material. In some aspects, the alkoxy phenol is wholly derived from a biological material. In other aspects, the phenol is partly derived from a biological material. In further aspects, the alkoxy phenol not derived from organic material that has been transformed by geological processes into petroleum, petrochemicals, and combinations thereof. In further aspects, the alkoxy phenol is from greater than 0 wt % to about 100 wt % derived from bio-based material, including exemplary wt % values of 1, 5, 10, 20, 30, 40, 50, 60, 70, 80, 90, and 99 wt. % derived from bio-based material. In still further aspects, the bio-based material comprises at least one lignocellulosic material, plant material, or a combination thereof. In yet further aspects, the bio-based material comprises at least one lignocellulosic material, plant material, or a combination thereof. In even further aspects, bio-based material is a bio-based oil, pyrolysis oil, or lignin-rich waste from a biorefinery.

In some aspects, the ketone comprises a C3-C26 ketone. In further aspects, the ketone comprises a C6-C12 cyclic ketone. In still further aspects, the ketone is acetone.

In some aspects, the ketone will have less than 1 wt % aldehyde impurity for example less than 1% acetaldehyde, propionaldehyde, benzaldehyde, formaldehyde or the like. In other aspects, the ketone will have less than 0.1 wt % aldehyde impurity. In further aspects, the phenol and ketone are provided at a molar ratio of at least about 2:1. In still further aspects, the phenol and ketone are provided at a molar ratio of from about 2:1 to about 20:1, including exemplary molar ratios of 3:1, 4:1, 5:1, 6:1, 7:1, 8:1, 9:1, 10:1, 11:1. 12:1, 13:1, 14:1, 15:1, 16:1, 17:1, 18:1, and 19:1.

In further aspects, conditions effective comprise reacting the phenol and ketone in the presence of a catalyst. In still further aspects, the catalyst can comprise $H_2SO_4$, an ion exchange resin catalyst, an cationic acidic ion exchange resin, a sulfonated polystyrene resin catalyst cross linked with divinyl benzene, trifluoro acetic acid, toluene sulfonic acid, trifluoromethane sulfonic acid, dodecyl benzene sulfonic acid (DBSA), HCl, or a combination thereof. In some aspects, the catalyst is $H_2SO_4$, an ion exchange resin catalyst, C1-C24 alkyl or alkyl aryl sulfonic acid, HCl, or a combination thereof. In other aspects, the catalyst is HCl. In further aspects, conditions effective comprise reacting the phenol and acetone in the presence of a promoter and acidic catalyst. In further aspects, the promoter can comprise 3-mercaptopropionic acid (3-MPA) or other mercapto carboxylic acids.

In further aspects, the catalyst can comprise a solid acid catalyst, such as, for example, sulfonated Zirconia, or acidified clays or an ion exchange resin or a combination thereof. In still further aspects, the catalyst can comprise promoters comprising compounds containing a mercapto group including alkylmercaptans, such as, methylmercaptan, ethylmercaptan, propylmercaptan, butylmercaptan, octylmercaptan, dodecylmercaptan, and the like; aromatic mercaptans, such as, thiophenol, thiocresol, and the like; mercapto organic acids, such as, mercapto acetic acid(thioglycolic acid), mercaptopropionic acid, and the like. In yet further aspects, the promoter is used along with an acid catalyst.

In further aspects, the amount of catalyst loading is generally in the range of about 0.1 to about 100 wt % relative to the total amount of phenol and ketone.

In further aspects, the amount of Concentrated HCl loading is generally in the range of about 01 to about 100 wt % relative to the total amount of phenol and ketone.

In further aspects, the amount of promoter loading is generally in the range of about 0.01 to about 10 wt % relative to the total amount of phenol and ketone.

In further aspects, conditions effective comprise adjusting the temperature to at least about 50° C. In still further aspects, the temperature is adjusted to a temperature of from 50° C. to about 150° C., including exemplary temperatures of about 55, 60, 65, 70, 75, 80, 85, 90, 95, 100, 105, 110, 115, 120, 125, 130, 135, 140, and 145° C.

In further aspects, conditions effective comprise maintaining the reaction for at least about 2 hours. In still further aspects, the reaction is maintained for about 1 to about 10 hours, including exemplary times of 2, 3, 4, 5, 6, 7, 8, and 9 hours.

In further aspects, the alkoxy bisphenol monomer of the reaction product is an ortho alkoxy bisphenol monomer. In still further aspects, the bisphenol monomer is PBMP, represented by the structure:

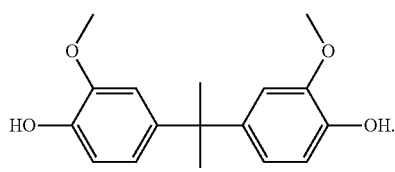 [SMILES: COc1cc(C(C)(C)c2ccc(O)c(OC)c2)ccc1O]

In further aspects, the reaction product comprises at least about 10 wt % of the alkoxy bisphenol monomer. In still further aspects, the reaction product comprises from at least about 1 wt % to about 100 wt % of alkoxy bisphenol monomer, including exemplary wt % of 5, 10, 15, 20, 25, 30, 35, 40, 45, 50, 55, 60, 65, 70, 75, 80, 85, 90, and 95 wt %. In yet further aspects, the reaction product comprises at least about 10 wt % of PBMP. In even further aspects, the reaction product comprises from at least about 10 wt % to about 100 wt % of PBMP, including exemplary wt % of 20, 25, 30, 35, 40, 45, 50, 55, 60, 65, 70, 75, 80, 85, 90, and 95 wt %. In still further aspects, the reaction product comprises at least about 10 wt % of the PBMP. In yet further aspects, the reaction product comprises from at least about 10 wt % to about 100 wt % of PBMP, including exemplary wt % of 20, 25, 30, 35, 40, 45, 50, 55, 60, 65, 70, 75, 80, 85, 90, and 95 wt %.

In various aspects, the invention provides a method for preparing an alkoxy bisphenol monomer, the method comprising: providing guaiacol; providing acetone; and reacting the guaiacol and acetone in the presence of an acidic catalyst under conditions effective to provide a reaction product comprising 4,4'(2,2'-isopropylidene)-bis(ortho methoxy)phenol (PBMP); wherein the PBMP does not exhibit a half maximal inhibitory concentration ($IC_{50}$) less than 0.00025M for alpha or beta in vitro estradiol receptors.

In further aspects, the compounds of this invention can be prepared by employing reactions as shown in the disclosed schemes, in addition to other standard manipulations that are known in the literature, exemplified in the experimental sections or clear to one skilled in the art. The following examples are provided so that the invention might be more fully understood, are illustrative only, and should not be construed as limiting. For clarity, examples having a fewer substituent can be shown where multiple substituents are allowed under the definitions disclosed herein.

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed compositions, methods, and uses.

1. Synthesis Scheme 1

In various aspects, ortho alkoxy bisphenol monomers of the present invention can be prepared generically by the synthetic scheme as shown below:

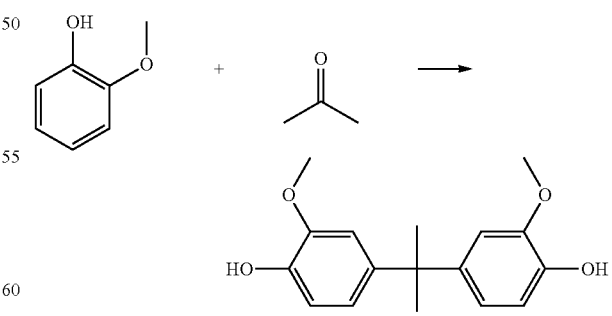

In further aspects, as shown in Scheme I, guaiacol and acetone is converted to PBMP in the presence of a catalyst.

Compounds are represented in generic form, with substituents as noted in compound descriptions elsewhere herein. More specific examples of scheme 1 are set forth below.

13 a. SYNTHESIS ROUTE 1

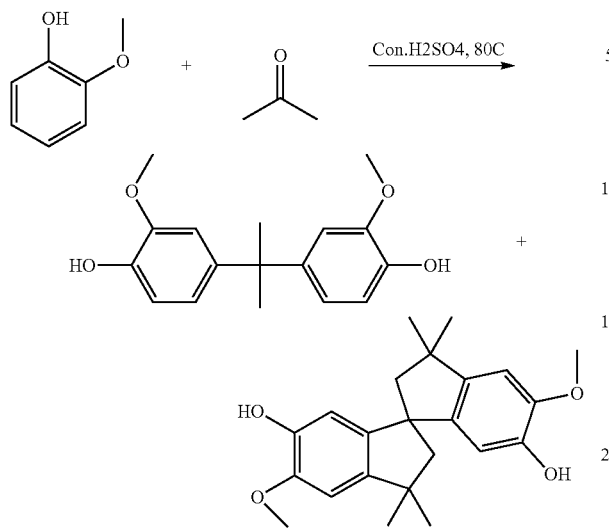

As shown in route 1, guaiacol and acetone are reacted in the presence of $H_2SO_4$ catalyst to produce PBMP, isomeric, and cyclic products such as, for example, guaiacol spirobiindane (G-SBI).

b. SYNTHESIS ROUTE 2

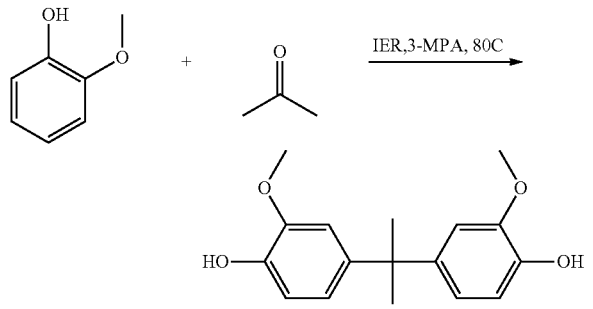

As shown in route 2, PBMP is synthesized using guaiacol and acetone (3:1 molar ratio) in presence of an ion exchange resin (IER) catalyst. In another aspect, the catalyst can be a sulfonated polystyrene resin cross linked with divinyl benzene.

c. SYNTHESIS ROUTE 3

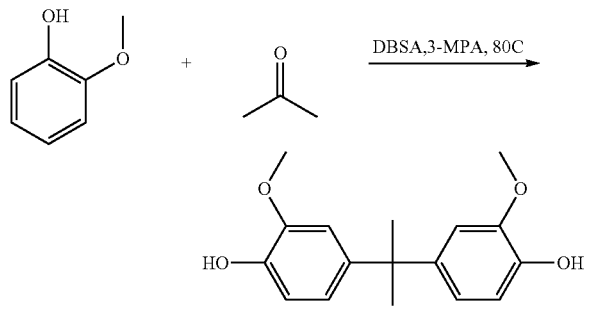

As shown in route 3, PBMP is synthesized using guaiacol and acetone (3:1 molar ratio) in presence of DBSA (dodecyl benzene sulfonic acid) catalyst.

d. SYNTHESIS ROUTE 4

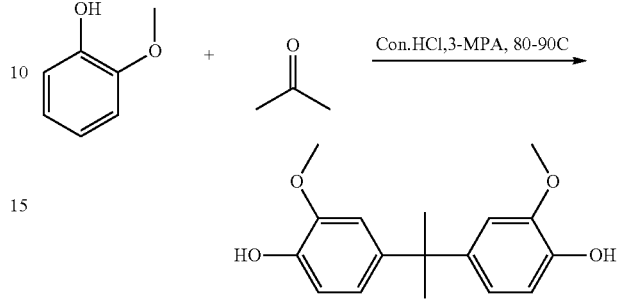

As shown in route 4, PBMP is synthesized using guaiacol and acetone (6:1 molar ratio) in presence of a HCl catalyst.

Intermediates and the product formation were confirmed by LCMS, NMR, and purity by HPLC.

D. METHODS OF MAKING POLYCARBONATE COMPOSITIONS

In various aspects, the disclosed alkoxy bisphenol monomers are useful for making alkoxy polycarbonate polymers and thermoplastic compositions.

In one aspect, the thermoplastic compositions comprise an alkoxy polycarbonate polymer composition wherein the alkoxy polycarbonate polymer comprises PBMP an alkoxy polycarbonate copolymer, or combinations thereof.

In a further aspect, the polycarbonate, when subjected to conditions effective to result in degradation, such as for example conditions effective for thermolysis or hydrolysis of the polycarbonate, do not produce degradants exhibiting significant estradiol like binding activity. In a still further aspect, the lack of significant estradiol like binding activity of these degradation products can be characterized by a determination of their half maximal inhibitory concentration ($IC_{50}$) for alpha or beta in vitro estradiol receptors. In one aspect, degradation products derived from alkoxy polycarbonates of the invention do not exhibit a half maximal inhibitory concentration ($IC_{50}$) less than 0.00025M for alpha or beta in vitro estradiol receptors. In a further aspect, degradation products derived from polycarbonates of the invention do not exhibit a half maximal inhibitory concentration ($IC_{50}$) less than 0.0003M, 0.00035M, 0.0004M, 0.00045M, 0.0005M, 0.00075M, or even 0.001M, for alpha or beta in vitro estradiol receptors. In a still further aspect, degradation products derived from alkoxy polycarbonates of the invention do not exhibit any identifiable half maximal inhibitory concentration ($IC_{50}$) greater than or equal to about 0.00025M, 0.0003M, 0.00035M, 0.0004M, 0.00045M, 0.0005M, 0.00075M, or even 0.001M, for alpha and/or beta in vitro estradiol receptors.

In one aspect, an alkoxy polycarbonate can comprise any method of polycarbonate polymerization, for example, as recited in U.S. Pat. No. 7,786,246, which is hereby incorporated in its entirety for the specific purpose of disclosing various polycarbonate methods. The term polycarbonate can be further defined as compositions have repeating structural units of the formula (1):

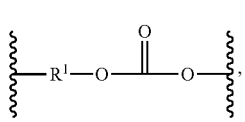

(1)

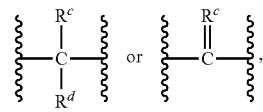

(5)

in which at least 60 percent of the total number of $R^1$ groups are aromatic organic radicals and the balance thereof are aliphatic, alicyclic, or aromatic radicals. In a further aspect, each $R^1$ is an aromatic organic radical and, more preferably, a radical of the formula (2):

$$-A^1-Y^1-A^2- \qquad (2),$$

wherein each of $A^1$ and $A^2$ is a monocyclic divalent aryl radical and $Y^1$ is a bridging radical having one or two atoms that separate $A^1$ from $A^2$. In various aspects, one atom separates $A^1$ from $A^2$. For example, radicals of this type include, but are not limited to, radicals such as —O—, —S—, —S(O)—, —S(O$_2$)—, —C(O)—, methylene, cyclohexylmethylene, 2-[2.2.1]-bicycloheptylidene, ethylidene, isopropylidene, neopentylidene, cyclohexylidene, cyclopentadecylidene, cyclododecylidene, and adamantylidene. The bridging radical $Y^1$ is preferably a hydrocarbon group or a saturated hydrocarbon group such as methylene, cyclohexylidene, or isopropylidene.

In a further aspect, polycarbonates can be produced by the interfacial reaction of dihydroxy compounds having the formula HO—$R^1$—OH, which includes dihydroxy compounds of formula (3):

$$HO-A^1-Y^1-A^2-OH \qquad (3),$$

wherein $Y^1$, $A^1$ and $A^2$ are as described above. Also included are bisphenol compounds of general formula (4):

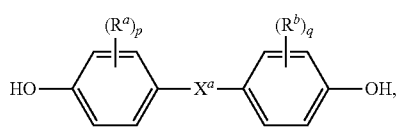

(4)

wherein $R^a$ and $R^b$ each represent an alkoxy group, or a monovalent hydrocarbon group and can be the same or different; p and q are each independently integers from 0 to 4; and $X^a$ is a bridging group connecting the two hydroxy-substituted aromatic groups, where the bridging group and the hydroxy substituent of each $C_6$ arylene group are disposed ortho, meta, or para (specifically para) to each other on the $C_6$ arylene group, for example, a single bond, —O—, —S—, —S(O)—, —S(O)$_2$—, —C(O)—, or a C3-C18 organic group, which can be cyclic or acyclic, aromatic or non-aromatic, and can further comprise heteroatoms such as halogens, oxygen, nitrogen, sulfur, silicon, or phosphorous. For example, according to further aspects, $X^a$ can be a substituted or unsubstituted C3-C18 cycloalkylidene; a C3-C25 alkylidene of the formula —C($R^c$)($R^d$)— wherein $R^c$ and $R^d$ are each independently hydrogen, C1-C12 alkyl, C1-C12 cycloalkyl, C7-C12 arylalkyl, C1-C12 heteroalkyl, or cyclic C7-C12 heteroarylalkyl; or a group of the formula —C(=$R^e$)— wherein $R^e$ is a divalent C1-C12 hydrocarbon group. In some aspects, $X^a$ represents one of the groups of formula (5):

wherein $R^c$ and $R^d$ each independently represent a hydrogen atom or a monovalent linear or cyclic hydrocarbon group and $R^e$ is a divalent hydrocarbon group.

According to various aspects of the present invention, the aromatic dihydroxy monomer comprising the polycarbonate does not exhibit a half maximal inhibitory concentration (IC$_{50}$) less than 0.00025M for alpha or beta in vitro estradiol receptors. According to further aspects, the aromatic dihydroxy monomers do not exhibit a half maximal inhibitory concentration (IC$_{50}$) less than 0.0003M, 0.00035M, 0.0004M, 0.00045M, 0.0005M, 0.00075M, or even 0.001M, for alpha or beta in vitro estradiol receptors. In still other embodiments, aromatic dihydroxy monomers do not exhibit any identifiable half maximal inhibitory concentration (IC$_{50}$) greater than or equal to about 0.00025M, 0.0003M, 0.00035M, 0.0004M, 0.00045M, 0.0005M, 0.00075M, or even 0.001M, for alpha and/or beta in vitro estradiol receptors.

In some aspects of the invention, suitable aromatic dihydroxy monomers comprise phenolic monomers. In further aspects, the phenolic monomers can comprise dihydric phenols, mono phenols, bisphenols, or a combination thereof.

In some aspects, the aromatic dihydroxy monomer is a bisphenolic monomer. In further aspects, the bisphenol monomer is an ortho alkoxy bisphenol monomer. In still further aspects, the ortho alkoxy bisphenol monomer has a structure represented by a formula:

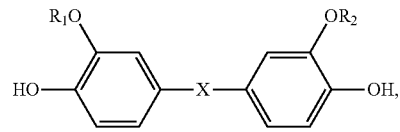

wherein each of R1 and R2 is independently selected from C1-C26 alkyl and C6-C26 alkaryl; and X is alkyl or aralkyl. In still further aspects, X can be a C3 to C16 hydrocarbon including, but not limited to cyclic hydrocarbons. In yet further aspects, each of R1 and R2 is independently selected from methyl, ethyl, propyl, octyl, isooctyl, benzyl, ethyl phenyl, butyl phenyl, propyl diphenyl, and cyclohexyl phenyl. In even further aspects, each of R1 and R2 is methyl. In even further aspects, X is selected from methylene, cyclohexylmethylene, 2-[2.2.1]-bicycloheptylidene, ethylidene, isopropylidene, neopentylidene, cyclohexylidene, cyclopentadecylidene, cyclododecylidene, and adamantylidene. In other aspects, X is selected from ethylidene, isopropylidene, isobutylidene neopentylidene, cyclohexylidene, alkyl substituted cyclohexylidene, aryl, cyclopentadecylidene, cyclododecylidene, sulfo, oxo, and bicycloheptylidene; and wherein each of R1 and R2 is independently selected from methyl, ethylidene, propylidene, butylidene, benzyl, phenyl, C1 to C4 alkyl phenyl, and cyclohexylidene In some aspects, the bisphenol monomer is 4,4'(2,2'-iso-Propylidene)-Bis(ortho Methoxy)Phenol (PBMP), and has a structure represented by the formula

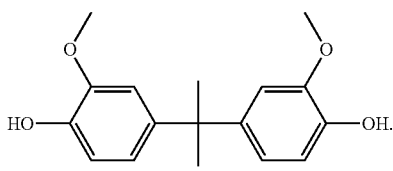 [SMILES: COc1cc(C(C)(C)c2ccc(O)c(OC)c2)ccc1O]

According to aspects of the disclosure, any additional suitable aromatic dihydroxy monomers exhibiting a lack of estradiol binding activity characterized by the half maximal inhibitory concentration values described above may be used. In further aspects, specific examples of suitable aromatic dihydroxy monomers include, without limitation, resorcinol, hydroquinone, methyl hydroquinone, t-butyl hydroquinone, di-t-butyl hydroquinones (DTBHQ), biphenols, tetramethyl bisphenol-A, spiro biindane bisphenols (SBIBP), or bis-(hydroxy aryl)-N-aryl isoindolinones. Combinations including at least one of the foregoing dihydroxy compounds with alkoxy bisphenols can also be used.

In addition to the polycarbonates described above, combinations of the polycarbonate with other thermoplastic polymers can be used.

In some aspects, the alkoxy polycarbonate can be a co-polycarbonate comprising repeating carbonate units derived from an ortho alkoxy bisphenol monomer and at least one additional phenolic monomer; and wherein the additional phenolic monomer does not exhibit a half maximal inhibitory concentration ($IC_{50}$) less than 0.00025M for alpha or beta in vitro estradiol receptors. In further aspects, the additional phenolic monomer comprises a bisphenolic monomer, a mono phenolic monomer, or a combination thereof. In still further aspects, the additional phenolic monomer comprises resorcinol, hydroquinone, methyl hydroquinone, t-butyl hydroquinone, di-t-butyl hydroquinones (DTBHQ), biphenols, tetramethyl bisphenol-A, spiro biindane bisphenols (SBIBP), bis-(hydroxy aryl)-N-aryl isoindolinones, hydrogenated bisphenol-A, 4,4'-(diphenylmethylene)diphenol, or a combination thereof.

In some aspects, the alkoxy polycarbonate is a co-polycarbonate comprising repeating carbonate units derived from an ortho alkoxy bisphenol monomer and at least one diol monomer; wherein the diol monomer does not exhibit a half maximal inhibitory concentration ($IC_{50}$) less than 0.00025M for alpha or beta in vitro estradiol receptors. In further aspects, the diol monomer comprises cyclohexanedimethanol, 2,2',4,4'-tetramethyl-1,3-cyclobutanediol, isosorbide, or a combination thereof.

In some aspects, the alkoxy polycarbonate is a poly(ester carbonate) comprising repeating carbonate units derived from the ortho alkoxy bisphenol monomer and at least one dicarboxylic acid monomer; wherein the dicarboxylic acid monomer does not exhibit a half maximal inhibitory concentration ($IC_{50}$) less than 0.00025M for alpha or beta in vitro estradiol receptors. In further aspects, the dicarboxylic acid monomer comprises isophthalic acid, terephthalic acid, a C6 to C36 aliphatic dicarboxylic acids, furan dicarboxylic acid, naphthalene dicarboxylic acid, sebacic acid, or a combination thereof.

In various further aspects, the alkoxy polycarbonate can employ two or more different dihydroxy compounds or a copolymer of a dihydroxy compounds with a glycol or with a hydroxy- or acid-terminated polyester or with a dibasic acid or hydroxy acid in the event a carbonate copolymer rather than a homopolymer is desired for use. Polyarylates and polyester-carbonate resins or their blends can also be employed. Branched polycarbonates are also useful, as well as blends of linear polycarbonate and a branched polycarbonate. The branched polycarbonates can be prepared by adding a branching agent during polymerization.

In a further aspect, the branching agents include polyfunctional organic compounds containing at least three functional groups selected from hydroxyl, carboxyl, carboxylic anhydride, haloformyl, and mixtures thereof. Specific examples include trimellitic acid, trimellitic anhydride, trimellitic trichloride, tris-p-hydroxy phenyl ethane, is a tin-bis-phenol, tris-phenol TC (1,3,5-tris((p-hydroxyphenyl)isopropyl)benzene), tris-phenol PA (4(4(1,1-bis(p-hydroxyphenyl)-ethyl) alpha, alpha-dimethyl benzyl)phenol), 4-chloroformyl phthalic anhydride, trimesic acid, and benzophenone tetracarboxylic acid. The branching agents can be added at a level of from 0.05-2.0 weight percent. Branching agents and procedures for making branched polycarbonates are described in U.S. Pat. Nos. 3,635,895 and 4,001,184. All types of polycarbonate end groups are contemplated as being useful in the thermoplastic composition, however, end groups derived from monomeric species with low biological activity, such as, for example, aliphatic alcohols, phenol, phenyl chloroformate, guaiacol (2-methoxy phenol), ortho alkoxy phenols and mixture thereof are preferred.

In a further aspect, the alkoxy polycarbonate can be a linear homopolymer derived from an ortho alkoxy bisphenol, in which each of $A^1$ and $A^2$ is PBMP and $Y^1$ is isopropylidene. The polycarbonates generally can have an intrinsic viscosity, as determined in chloroform at 25° C., of 0.3 to 1.5 deciliters per gram (dl/g), specifically 0.45 to 1.0 dl/g. The polycarbonates can have a weight average molecular weight (Mw) of 10,000 to 100,000 g/mol, as measured by gel permeation chromatography (GPC) using a crosslinked styrene-divinyl benzene column, at a sample concentration of 1 milligram per milliliter, and as calibrated with polycarbonate standards. In a yet further aspect, the polycarbonate has an Mw of about 15,000 to about 55,000. In an even further aspect, the polycarbonate has an Mw of about 18,000 to about 40,000.

In a further aspect, an alkoxy polycarbonate component used in the present invention can have a melt volume flow rate (often abbreviated MVR) measures the rate of extrusion of a thermoplastics through an orifice at a prescribed temperature and load. Alkoxy polycarbonates useful for the formation of articles can have an MVR, measured at 300° C. under a load of 1.2 kg according to ASTM D1238-04 or ISO 1133, of 0.5 to 80 cubic centimeters per 10 minutes (cc/10 min) In a still further aspect, the alkoxy polycarbonate, can have a MVR of 45 to 75 cc/10 min, specifically 50 to 70 cc/10 min, and more specifically 55 to 65 cc/10 min at 300° C. with a 1.2 Kg load.

Alkoxy polycarbonates can comprise copolymers comprising carbonate units and other types of polymer units, including ester units, and combinations comprising at least one of homopolycarbonates and copolycarbonates. An exemplary polycarbonate copolymer of this type is a polyester carbonate, also known as a polyester-polycarbonate or polyester carbonate. Such copolymers further contain carbonate units derived from oligomeric ester-containing dihydroxy compounds (also referred to herein as hydroxy end-capped oligomeric acrylate esters).

In various further aspects, "alkoxy polycarbonates" and "alkoxy polycarbonate resins" as used herein further include homopolycarbonates, copolymers comprising different $R^1$ moieties in the carbonate (referred to herein as "copolycarbonates"), copolymers comprising carbonate units and other types of polymer units, such as ester units, polysiloxane units, and combinations comprising at least one of homopolycarbonates and copolycarbonates. As used herein, "combination" is inclusive of blends, mixtures, alloys, reaction products, and the like.

In further aspects, the alkoxy polycarbonate has a glass transition temperature (Tg) of 110 to 145° C., specifically 115 to 145° C., more specifically 120 to 145° C., more specifically 120 to 139° C., and still more specifically 120 to 139° C.

In one aspect, the alkoxy polycarbonate polymers and compositions can be manufactured by processes such as interfacial polymerization and melt polymerization.

The alkoxy polycarbonate polymers and compositions disclosed herein can, in various aspects, be prepared by a melt polymerization process. Generally, in the melt polymerization process, polycarbonates are prepared by co-reacting, in a molten state, alkoxy bisphenol and other commoners, such as isosorbide, aliphatic diol and/or aliphatic diacid, and any additional dihydroxy compound, and a diaryl carbonate ester, such as diphenyl carbonate, or more specifically in an aspect, an activated carbonate such as bis(methyl salicyl)carbonate, in the presence of a transesterification catalyst. The reaction can be carried out in typical polymerization equipment, such as one or more continuously stirred reactors (CSTRs), plug flow reactors, wire wetting fall polymerizers, free fall polymerizers, wiped film polymerizers, BANBURY® mixers, single or twin screw extruders, or combinations of the foregoing. In one aspect, volatile monohydric phenol can be removed from the molten reactants by distillation and the polymer is isolated as a molten residue.

The conditions effective to provide the polycondensation reaction product typically comprise the presence of a polymerization catalyst.

In further aspects, the conditions effective can include a transesterification catalyst comprising a first catalyst, also referred to herein as an alpha catalyst, comprising a metal cation and an anion. In an aspect, the cation is an alkali or alkaline earth metal comprising Li, Na, K, Cs, Rb, Mg, Ca, Ba, Sr, or a combination comprising at least one of the foregoing. The anion is hydroxide (OH), superoxide ($O^2$), thiolate (HS), sulfide ($S^2$), a $C_{1-20}$ alkoxide, a $C_{6-20}$ aryloxide, a $C_{1-20}$ carboxylate, a phosphate including biphosphate, a $C_{1-20}$ phosphonate, a sulfate including bisulfate, sulfites including bisulfites and metabisulfites, a $C_{1-20}$ sulfonate, a carbonate including bicarbonate, or a combination comprising at least one of the foregoing. In another aspect, salts of an organic acid comprising both alkaline earth metal ions and alkali metal ions can also be used. Salts of organic acids useful as catalysts are illustrated by alkali metal and alkaline earth metal salts of formic acid, acetic acid, stearic acid and ethyelenediaminetetraacetic acid. The catalyst can also comprise the salt of a non-volatile inorganic acid. By "nonvolatile", it is meant that the referenced compounds have no appreciable vapor pressure at ambient temperature and pressure. In particular, these compounds are not volatile at temperatures at which melt polymerizations of polycarbonate are typically conducted. The salts of nonvolatile acids are alkali metal salts of phosphites; alkaline earth metal salts of phosphites; alkali metal salts of phosphates; and alkaline earth metal salts of phosphates. Exemplary transesterification catalysts include, lithium hydroxide, sodium hydroxide, potassium hydroxide, cesium hydroxide, magnesium hydroxide, calcium hydroxide, barium hydroxide, lithium formate, sodium formate, potassium formate, cesium formate, lithium acetate, sodium acetate, potassium acetate, lithium carbonate, sodium carbonate, potassium carbonate, lithium methoxide, sodium methoxide, potassium methoxide, lithium ethoxide, sodium ethoxide, potassium ethoxide, lithium phenoxide, sodium phenoxide, potassium phenoxide, sodium sulfate, potassium sulfate, $NaH_2PO_3$, $NaH_2PO_4$, $Na_2H_2PO_3$, $KH_2PO_4$, $CsH_2PO_4$, $Cs_2H_2PO_4$, $Na_2SO_3$, $Na_2S_2O_5$, sodium mesylate, potassium mesylate, sodium tosylate, potassium tosylate, magnesium disodium ethylenediamine tetraacetate (EDTA magnesium disodium salt), or a combination comprising at least one of the foregoing. It will be understood that the foregoing list is exemplary and should not be considered as limited thereto. In one aspect, the transesterification catalyst is an alpha catalyst comprising an alkali or alkaline earth salt. In an exemplary aspect, the transesterification catalyst comprising sodium hydroxide, potassium hydroxide, sodium carbonate, potassium carbonate, sodium methoxide, potassium methoxide, $NaH_2PO_4$, or a combination comprising at least one of the foregoing.

The amount of alpha catalyst can vary widely according to the conditions of the melt polymerization, and can be about 0.001 to about 500 μmol. In an aspect, the amount of alpha catalyst can be about 0.01 to about 20 μmol, specifically about 0.1 to about 10 μmol, more specifically about 0.5 to about 9 μmol, and still more specifically about 1 to about 7 μmol, per mole of aliphatic diol and any other dihydroxy compound present in the melt polymerization.

In another aspect, a second transesterification catalyst, also referred to herein as a beta catalyst, can optionally be included in the melt polymerization process, provided that the inclusion of such a second transesterification catalyst does not significantly adversely affect the desirable properties of the alkoxy polycarbonate. Exemplary transesterification catalysts can further include a combination of a phase transfer catalyst of formula $(R^3)_4Q^+X$ above, wherein each $R^3$ is the same or different, and is a $C_{1-10}$ alkyl group; Q is a nitrogen or phosphorus atom; and X is a halogen atom or a $C_{1-10}$ alkoxy group or $C_{6-18}$ aryloxy group. Exemplary phase transfer catalyst salts include, for example, $[CH_3(CH_2)_3]_4NX$, $[CH_3(CH_2)_3]_4PX$, $[CH_3(CH_2)_5]_4NX$, $[CH_3(CH_2)_6]_4NX$, $[CH_3(CH_2)_4]_4NX$, $CH_3[CH_3(CH_2)_3]_3NX$, and $CH_3[CH_3(CH_2)_2]_3NX$, wherein X is $Cr^-$, $Br^-$, a $C_{1-8}$ alkoxy group or a $C_{6-18}$ aryloxy group. Examples of such transesterification catalysts include tetrabutylammonium hydroxide, methyltributylammonium hydroxide, tetrabutylammonium acetate, tetrabutylphosphonium hydroxide, tetrabutylphosphonium acetate, tetrabutylphosphonium phenolate, or a combination comprising at least one of the foregoing. Other melt transesterification catalysts include alkaline earth metal salts or alkali metal salts. In various aspects, where a beta catalyst is desired, the beta catalyst can be present in a molar ratio, relative to the alpha catalyst, of less than or equal to 10, specifically less than or equal to 5, more specifically less than or equal to 1, and still more specifically less than or equal to 0.5. In other aspects, the melt polymerization reaction disclosed herein uses only an alpha catalyst as described hereinabove, and is substantially free of any beta catalyst. As defined herein, "substantially free of" can mean where the beta catalyst has been excluded from the melt polymerization reaction. In one aspect, the beta catalyst is present in an amount of less than about 10 ppm, specifically less than 1 ppm, more specifically less than about 0.1 ppm, more specifically less than or equal to about 0.01 ppm, and more specifically less than or equal to about 0.001 ppm, based on the total weight of all components used in the melt polymerization reaction. In further aspects, Any alpha or beta catalyst, or mixture thereof, should be free of any monomer that could have estradiol binding at least less than or equal to 2.5×E-4M. In other instances any thermal or hydrolytic decomposition product from the alpha or beta catalyst, or mixture thereof, should also show no estradiol binding at least less than or equal to 2.5×E-4 M.

In one aspect, an end-capping agent (also referred to as a chain-stopper) can optionally be used to limit molecular weight growth rate, and so control molecular weight in the alkoxy polycarbonate. In various aspects, many conventionally known end capping agents exhibit undesirably high levels of estradiol binding activity. In contrast, however, suitable end capping agents or chain stoppers for use with the present invention exhibit estradiol binding activity levels similar or even identical to that of the selected aromatic dihydroxy monomers. More specifically, the end capping agents suitable for use in the present invention also do not exhibit a half maximal inhibitory concentration ($IC_{50}$) less than 0.00025M for alpha or beta in vitro estradiol receptors. As such, a degradation product of the selected chain stopper will likewise not exhibit a half maximal inhibitory concentration ($IC_{50}$) less than 0.00025M for alpha or beta in vitro estradiol receptors. In further aspects, exemplary chain stoppers include certain mono-phenolic compounds, phenyl chloroformate and the like. In still further aspects, a suitable chain stopper for use in the present invention is phenol, phenyl chloroformate, or guaiacol (2-methoxyphenol), or a combination thereof. Thus, when phenol is included as a chain stopper, the resulting polycarbonate comprises phenol as an end cap to the polymer chain. It should be understood however that the polycarbonates disclosed herein can be produced having any desired molecular weight (Mw) with any end cap providing the end cap has a half maximal inhibitory concentration ($IC_{50}$) less than 0.00025M for alpha or beta in vitro estradiol receptors. In a further aspect, end groups derived from monomeric specifies with low biological activity, for example; aliphatic alcohols, phenol, phenyl chloroformate, guaiacol (2-methoxy phenol), ortho alkoxy phenols and mixtures thereof are preferred.

In one aspect, the melt polymerization reaction can be conducted by subjecting the reaction mixture to a series of temperature-pressure-time protocols. In some aspects, this involves gradually raising the reaction temperature in stages while gradually lowering the pressure in stages. In one aspect, the pressure is reduced from about atmospheric pressure at the start of the reaction to about 1 millibar (100 Pa) or lower, or in another aspect to 0.1 millibar (10 Pa) or lower in several steps as the reaction approaches completion. The temperature can be varied in a stepwise fashion beginning at a temperature of about the melting temperature of the reaction mixture and subsequently increased to final temperature. In one aspect, the reaction mixture is heated from room temperature to about 150° C. In such an aspect, the polymerization reaction starts at a temperature of about 150° C. to about 220° C. In another aspect, the polymerization temperature can be up to about 220° C. In other aspects, the polymerization reaction can then be increased to about 250° C. and then optionally further increased to a temperature of about 320° C., and all sub ranges there between. In one aspect, the total reaction time can be from about 30 minutes to about 200 minutes and all sub ranges there between. This procedure will generally ensure that the reactants react to give polycarbonates with the desired molecular weight, glass transition temperature and physical properties. The reaction proceeds to build the polycarbonate chain with production of ester-substituted alcohol by-product such as methyl salicylate. In one aspect, efficient removal of the by-product can be achieved by different techniques such as reducing the pressure. Generally the pressure starts relatively high in the beginning of the reaction and is lowered progressively throughout the reaction and temperature is raised throughout the reaction.

In one aspect, the progress of the reaction can be monitored by measuring the melt viscosity or the weight average molecular weight of the reaction mixture using techniques known in the art such as gel permeation chromatography. These properties can be measured by taking discrete samples or can be measured on-line. After the desired melt viscosity and/or molecular weight is reached, the final polycarbonate product can be isolated from the reactor in a solid or molten form. It will be appreciated by a person skilled in the art, that the method of making an alkoxy polycarbonate and alkoxy copolycarbonates as described in the preceding sections can be made in a batch or a continuous process and the process disclosed herein is preferably carried out in a solvent free mode. Reactors chosen should ideally be self-cleaning and should minimize any "hot spots." However, vented extruders similar to those that are commercially available can be used.

Alkoxy polycarbonates, including alkoxy polyester-polycarbonates, can be also be manufactured by interfacial polymerization. Although the reaction conditions for interfacial polymerization can vary, an exemplary process generally involves dissolving or dispersing a dihydric phenol reactant in aqueous caustic soda or potash, adding the resulting mixture to a suitable water-immiscible solvent medium, and contacting the reactants with a carbonate precursor in the presence of a catalyst such as triethylamine or a phase transfer catalyst, under controlled pH conditions, e.g., about 8 to about 10. The most commonly used water immiscible solvents include methylene chloride, 1,2-dichloroethane, chlorobenzene, toluene, and the like.

Carbonate precursors include, for example, a carbonyl halide such as carbonyl bromide or carbonyl chloride, or a haloformate such as a bishaloformates of a dihydric phenol (e.g., the bischloroformates of bisphenol A, hydroquinone, or the like) or a glycol (e.g., the bishaloformate of ethylene glycol, neopentyl glycol, polyethylene glycol, or the like). Combinations comprising at least one of the foregoing types of carbonate precursors can also be used. In an exemplary aspect, an interfacial polymerization reaction to form carbonate linkages uses phosgene as a carbonate precursor, and is referred to as a phosgenation reaction.

An effective amount of a phase transfer catalyst can be about 0.1 to about 10 wt % based on the weight of bisphenol in the phosgenation mixture. In another aspect, an effective amount of phase transfer catalyst can be about 0.5 to about 2 wt % based on the weight of bisphenol in the phosgenation mixture. In an interfacial polymerization phase transfer catalysts such as such as tetra alkyl phosphonium, tetra alkyl ammonium or tri alkyl amine compounds may be used. In some instances C1 to C6 trialkyl amines may be used, in other instances triethyl amine (TEA) may be employed.

In various aspects, the alkoxy polycarbonate comprises at least one alkoxy polycarbonate polymer, wherein the alkoxy polycarbonate polymer can be a homopolymer, a copolymer, or combinations thereof. In a further aspect, the alkoxy polycarbonate comprises two or more alkoxy polycarbonate polymers. In a still further aspect, the alkoxy polycarbonate comprises three or more alkoxy polycarbonate polymers. In a yet further aspect, the alkoxy polycarbonate is a blend of at least two alkoxy polycarbonate polymers.

In a further aspect, the alkoxy polycarbonate is a homopolymer. In a still further aspect, the polycarbonate is a homopolymer comprising repeating units derived from 4,4' (2,2'-isopropylidene)-bis(ortho methoxy)phenol (PBMP).

In a further aspect, the alkoxy polycarbonate is a copolymer. In a still further aspect, the alkoxy polycarbonate is a copolymer comprising repeating units derived from PBMP. In yet a further aspect, the alkoxy polycarbonate is a copolymer comprising repeating units derived from sebacic acid. In an even further aspect, the alkoxy polycarbonate is a copolymer comprising repeating units derived from sebacic acid and PBMP.

In a further aspect, an alkoxy polycarbonate is disclosed wherein the repeating carbonate units are derived from PBMP as aromatic dihydroxy monomers. In a still further aspect, the resulting alkoxy polycarbonate structure is shown below, wherein "n" can be any desired integer based upon the desired chain length for the polycarbonate

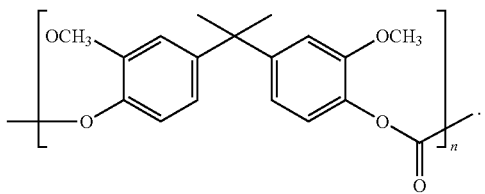

In a further aspect, the alkoxy polycarbonate has a weight average molecular weight from about 15,000 to about 50,000 grams/mole, as measured by gel permeation chromatography using BPA polycarbonate standards. In a still further aspect, the polycarbonate has a weight average molecular weight from about 15,000 to about 40,000 grams/mole, as measured by gel permeation chromatography using BPA polycarbonate standards. In yet a further aspect, the alkoxy polycarbonate has a weight average molecular weight from about 17,000 to about 50,000 grams/mole, as measured by gel permeation chromatography using BPA polycarbonate standards. In an even further aspect, the polycarbonate has a weight average molecular weight from about 17,000 to about 40,000 grams/mole, as measured by gel permeation chromatography using BPA polycarbonate standards.

In a further aspect, the alkoxy polycarbonate comprises a copolymer.

In a further aspect, the alkoxy polycarbonate comprises a blend of at least two polycarbonate polymers.

In a further aspect, the alkoxy polycarbonate comprises PBMP in an amount from about 10 wt % to about 100 wt % of the polycarbonate. In a still further aspect, the polycarbonate comprises PBMP in an amount from about 20 wt % to about 90 wt % of the polycarbonate. In yet a further aspect, the alkoxy polycarbonate comprises PBMP in an amount from about 20 wt % to about 85 wt % of the alkoxy polycarbonate. In an even further aspect, the alkoxy polycarbonate comprises PBMP in an amount from about 20 wt % to about 80 wt % of the polycarbonate. In a still further aspect, the polycarbonate comprises PBMP in an amount from about 20 wt % to about 75 wt % of the alkoxy polycarbonate. In yet a further aspect, the polycarbonate comprises PBMP in an amount from about 20 wt % to about 70 wt % of the polycarbonate. In a still further aspect, the polycarbonate comprises PBMP in an amount from about 20 wt % to about 65 wt % of the polycarbonate. In yet a further aspect, the polycarbonate comprises PBMP in an amount from about 20 wt % to about 60 wt % of the polycarbonate. In an even further aspect, the polycarbonate comprises PBMP in an amount from about 20 wt % to about 55 wt % of the polycarbonate. In a still further aspect, the polycarbonate comprises PBMP in an amount from about 20 wt % to about 50 wt % of the alkoxy polycarbonate. In yet a further aspect, the polycarbonate comprises PBMP in an amount from about 20 wt % to about 45 wt % of the polycarbonate.

In various aspects, the disclosed alkoxy polycarbonate thermoplastic compositions further comprise at least one additive material ordinarily incorporated in polycarbonate resin compositions of this type, with the proviso that the additives are selected so as to not significantly adversely affect the desired properties of the alkoxy polycarbonate composition. Combinations of additives can be used. Such additives can be mixed at a suitable time during the mixing of the components for forming the composition. Exemplary and non-limiting examples of additive materials that can be present in the disclosed polycarbonate compositions include an acid scavenger, anti-drip agent, antioxidant, antistatic agent, chain extender, colorant (e.g., pigment and/or dye), de-molding agent, flow promoter, lubricant, mold release agent, plasticizer, quenching agent, stabilizer (including for example, a thermal stabilizer, a hydrolytic stabilizer, or a light stabilizer), or UV additive (including for example, absorbing additive or UV reflecting additive), or a combination thereof. In further aspects, each of the at least one additive does not exhibit a half maximal inhibitory concentration ($IC_{50}$) less than 0.00025M for alpha or beta in vitro estradiol receptors.

In further aspects, the additive can comprise a phosphorous-containing compound, such as a phosphite, phosphonate or a phosphate. In some aspects, the one or more additive comprises a phosphite and wherein when the phosphite is subjected to conditions effective to provide one or more phosphite hydrolysis product, each of the one or more phosphite hydrolysis products does not exhibit a half maximal inhibitory concentration ($IC_{50}$) less than 0.00025M for alpha or beta in vitro estradiol receptors. In further aspects, the phosphite comprises a diphenyl alkyl phosphite, phenyl dialkyl phosphite, trialkyl phosphite, dialkyl phosphite, triphenyl phosphite, diphenyl pentaerythritol diphosphite, or any combination thereof. In other aspects, the additive comprises at least one phosphorus compound, and wherein when the phosphorous is subjected to conditions effective to provide at least one phosphorous compound hydrolysis product, each of the at least one phosphorous compound hydrolysis product does not exhibit a half maximal inhibitory concentration ($IC_{50}$) less than 0.00025M for alpha or beta in vitro estradiol receptors. In further aspects, the phosphorus compound comprises an aryl phosphate comprising triphenyl phosphate, resorcinol phenyl diphosphate, spirobiindane phenyl diphosphate, di-tertbutyl hydroquinone phenyl diphosphate, biphenol phenyl diphosphate, hydroquinone phenyl diphosphate, or a combination thereof.

According to aspects of the disclosure, the amount of phosphorous-containing compound compounded with the polycarbonate is an amount sufficient to result in the desired effect for which the additive is intended. For example, if the additive is a flame retardant the amount of additive will be that amount sufficient to provide a desired level of flame retardance. Such amounts can be readily determined by one of ordinary skill in the art without undue experimentation. In some aspects, where the phosphorous-containing compound is a phosphite, phosphonate or combination thereof, it is present in an amount in the range of 0.0001 to 2.0 wt %. based on the parts by weight of the polycarbonate.

In a further aspect, UV additives can be added, and comprise benzotriazoles, benzophenones, cyanoacrylates, triazines, oxanilides, hindered amines and mixtures thereof. In some aspects, benzotriazoles are preferred.

In a further aspect, the antioxidant is a primary antioxidant, a secondary antioxidant, or combinations thereof. In a still further aspect, the primary antioxidant is selected from a hindered phenol alone or in a combination with other antioxidants. In yet a further aspect, the hindered phenol comprises one or more compounds selected from triethylene glycol bis[3-(3-t-butyl-5-methyl-4-hydroxyphenyl)propionate], 1,6-hexanediolbis[3-(3,5-di-t-butyl-4-hydroxyphenyl)propionate], 2,4-bis(n-octylthio)-6-(4-hydroxy-3,5-di-t-butylanilino)-1,3,5-triazine, pentaerythrityl tetrakis[3-(3,5-di-t-butyl-4-hydroxyphenyl)propionate], 2,2-thiodiethylene bis[3-(3,5-di-t-butyl-4-hydroxyphenyl)propionate], octadecyl 3-(3,5-di-t-butyl-4-hydroxyphenyl)propionate, N,N'-hexamethylene bis(3,5-di-t-butyl-4-hydroxy-hydrocinnamide), tetrakis(methylene 3,5-di-tert-butyl-hydroxycinnamate) methane, and octadecyl 3,5-di-tert-butylhydroxyhydrocinnamate. In an even further aspect, the hindered phenol comprises octadecyl-3-(3,5-di-t-butyl-4-hydroxyphenyl)-propionate.

In a further aspect, the hindered phenol anti-oxidant is present in an amount from about 0.01 wt % to about 0.50 wt %. In a still further aspect, the primary anti-oxidant is present in an amount from about 0.01 wt % to about 0.40 wt %. In yet a further aspect, the primary anti-oxidant is present in an amount from about 0.01 wt % to about 0.20 wt %. In an even further aspect, the hindered anti-oxidant is present in an amount from about 0.01 wt % to about 0.15 wt %. In a still further aspect, the primary anti-oxidant is present in an amount from about 0.03 wt % to about 0.50 wt %. In yet a further aspect, the hindered phenol anti-oxidant is present in an amount from about 0.05 wt % to about 0.50 wt %. In an even further aspect, the hindered phenol anti-oxidant is present in an amount from about 0.05 wt % to about 0.40 wt %. In a still further aspect, the hindered phenol anti-oxidant is present in an amount from about 0.05 wt % to about 0.20 wt %. In yet a further aspect, the hindered phenol anti-oxidant is present in an amount from about 0.05 wt % to about 0.15 wt %.

In a further aspect, the further anti-oxidant is selected from an organophosphate and thioester, or a combination thereof. In a still further aspect, the secondary anti-oxidant comprises one or more compounds selected from tetrakis(2,4-di-tert-butylphenyl) [1,1-biphenyl]-4,4'-diylbisphosphonite, tris(2,4-di-tert-butylphenyl) phosphite, bis(2,4-di-tert-butylphenyl) pentaerythritol diphosphite, bis(2,4-dicumylphenyl) pentaerythritol diphosphite, tris(nonyl phenyl)phosphite, and distearyl pentaerythritol diphosphite. In yet a further aspect, the secondary anti-oxidant comprises tris(2,4-di-tert-butylphenyl) phosphite.

In a further aspect, the secondary further anti-oxidant is present in an amount from about 0.01 wt % to about 0.50 wt %. In a still further aspect, the secondary anti-oxidant is present in an amount from about 0.01 wt % to about 0.40 wt %. In yet a further aspect, the secondary anti-oxidant is present in an amount from about 0.01 wt % to about 0.20 wt %. In an even further aspect, the secondary anti-oxidant is present in an amount from about 0.01 wt % to about 0.15 wt %. In a still further aspect, the secondary anti-oxidant is present in an amount from about 0.03 wt % to about 0.50 wt %. In yet a further aspect, the secondary anti-oxidant is present in an amount from about 0.05 wt % to about 0.50 wt %. In an even further aspect, the secondary anti-oxidant is present in an amount from about 0.05 wt % to about 0.40 wt %. In a still further aspect, the secondary anti-oxidant is present in an amount from about 0.05 wt % to about 0.20 wt %. In yet a further aspect, the secondary anti-oxidant is present in an amount from about 0.05 wt % to about 0.15 wt %. In an even further aspect, phenyl, alkyl and alkyl phenyl phosphite, if present, the parent phenolic component of the phosphite generated through degradation (for example phenol generated by hydrolysis), do not exhibit any identifiable half maximal inhibitory concentration ($IC_{50}$) greater than or equal to about 0.00025M, 0.0003M, 0.00035M, 0.0004M, 0.00045M, 0.0005M, 0.00075M, or even 0.001M, for alpha and/or beta in vitro estradiol receptors. Non-limiting examples of such phosphites include: triphenyl phosphite, tridecyl phosphite, phenyl dioctyl phosphite, diphenyl isodecyl phosphite and any mixture thereof.

In a further aspect, suitable thermal stabilizer additives include, for example, organic phosphites such as triphenyl phosphite, tris-(2,6-dimethylphenyl)phosphite, tris-(mixed mono- and di-nonylphenyl)phosphite or the like; phosphonates such as dimethylbenzene phosphonate or the like, organic phosphates such as trimethyl phosphate, thioesters such as pentaerythritol betalaurylthiopropionate, and the like, or combinations comprising at least one of the foregoing thermal stabilizers.

Thermal stabilizers are generally used in amounts of about 0.01 wt % to about 5 wt %, optionally about 0.05 wt % to about 2.0 wt % of the polycarbonate composition. In one aspect, the thermal stabilizer is present in an amount from about 0.01 wt % to about 3.0 wt %. In another aspect, the thermal stabilizer is present in an amount from about 0.01 wt % to about 2.5 wt %. In still another aspect, the thermal stabilizer is present in an amount from about 0.5 wt % to about 2.5 wt %. In still another aspect, the thermal stabilizer is present in an amount from about 0.5 wt % to about 2.0 wt %. In still another aspect, the thermal stabilizer is present in an amount from about 0.1 wt % to about 0.8 wt %. In still another aspect, the thermal stabilizer is present in an amount from about 0.1 wt % to about 0.7 wt %. In still another aspect, the thermal stabilizer is present in an amount from about 0.1 wt % to about 0.6 wt %. In still another aspect, the thermal stabilizer is present in an amount from about 0.1 wt % to about 0.5 wt %. In still another aspect, the thermal stabilizer is present in an amount from about 0.1 wt % to about 0.4 wt %. In still another aspect, the thermal stabilizer is present in an amount from about 0.05 wt % to about 1.0 wt %.

In various aspects, plasticizers, lubricants, and/or mold release agents additives can also be used. There is a considerable overlap among these types of materials, which include, for example, phthalic acid esters such as dioctyl-4,5-epoxy-hexahydrophthalate; tris(octoxycarbonylethyl)isocyanurate; tristearin; di- or polyfunctional aromatic phosphates such as resorcinol tetraphenyl diphosphate (RDP), the bis(diphenyl) phosphate of hydroquinone and the bis(diphenyl)phosphate of bisphenol-A; poly-alpha-olefins; epoxidized soybean oil; silicones, including silicone oils; esters, for example, fatty acid esters such as alkyl stearyl esters, e.g. methyl stearate; stearyl stearate, glycerol mono stearate, pentaerythritol tetrastearate, and the like; mixtures of methyl stearate and hydrophilic and hydrophobic nonionic surfactants comprising polyethylene glycol polymers, polypropylene glycol polymers, and copolymers thereof; waxes such as beeswax, montan wax, paraffin wax or the like.

Thermoplastic composition additives such as plasticizers, lubricants, and/or mold release agents additive are generally used in amounts of about 0.01 wt % to about 20 wt %, optionally about 0.5 wt % to about 10 wt % the alkoxy polycarbonate blend composition. In one aspect, the mold release agent is methyl stearate; stearyl stearate or pentaerythritol tetrastearate. In another aspect, the mold release agent is pentaerythritol tetrastearate.

In various aspects, the mold release agent is present in an amount from about 0.01 wt % to about 3.0 wt %. In another aspect, the mold release agent is present in an amount from about 0.01 wt % to about 2.5 wt %. In still another aspect, the mold release agent is present in an amount from about 0.5 wt % to about 2.5 wt %. In still another aspect, the mold release agent is present in an amount from about 0.5 wt % to about 2.0 wt %. In still another aspect, the mold release agent is present in an amount from about 0.1 wt % to about 0.6 wt %. In still another aspect, the mold release agent is present in an amount from about 0.1 wt % to about 0.5 wt %.

In a further aspect, the anti-drip agents can also be present. In a further aspect, the anti-drip agent is a styrene-acrylonitrile copolymer encapsulated polytetrafluoroethylene. Exemplary anti-drip agents can include a fibril forming or non-fibril forming fluoropolymer such as polytetrafluoroethylene (PTFE). The anti-drip agent can optionally be encapsulated by a rigid copolymer, for example styrene-acrylonitrile (SAN). PTFE encapsulated in SAN is known as TSAN. Encapsulated fluoropolymers can be made by polymerizing the encapsulating polymer in the presence of the fluoropolymer, for example, in an aqueous dispersion. TSAN can provide significant advantages over PTFE, in that TSAN can be more readily dispersed in the composition. A suitable TSAN can comprise, for example, about 50 wt % PTFE and about 50 wt % SAN, based on the total weight of the encapsulated fluoropolymer. Alternatively, the fluoropolymer can be pre-blended in some manner with a second polymer, such as for, example, an aromatic polycarbonate resin or SAN to form an agglomerated material for use as an anti-drip agent. Either method can be used to produce an encapsulated fluoropolymer.

In a further aspect, the anti-drip agent is present in an amount from about 0.01 wt % to about 2 wt %. In a still further aspect, the anti-drip agent is present in an amount from about 0.01 wt % to about 1.5 wt %. In yet a further aspect, the anti-drip agent is present in an amount from about 0.01 wt % to about 1.0 wt %.

In various aspects, the thermoplastic compositions of the present invention can further comprise an acid or an acid salt. In one aspect, the acid or acid salt is an inorganic acid or inorganic acid salt. In one aspect, the acid is an acid including a phosphorous containing oxy-acid. In one aspect, the phosphorous containing oxy-acid is a multi-protic phosphorus containing oxy-acid having the general formula:

$H_m P_t O_n$, where m and n are each 2 or greater and t is 1 or greater. Examples of the acids of the foregoing formula include, but are not limited to, acids represented by the following formulas: $H_3PO_4$, $H_3PO_3$, and $H_3PO_2$. Other exemplary acids include phosphoric acid, phosphorous acid, hypophosphorous acid, hypophosphoric acid, phosphinic acid, phosphonic acid, metaphosphoric acid, hexametaphosphoric acid, thiophosphoric acid, fluorophosphoric acid, difluorophosphoric acid, fluorophosphorous acid, difluorophosphorous acid, fluorohypophosphorous acid, or fluorohypophosphoric acid. Alternatively, acids and acid salts, such as, for example, sulfuric acid, sulfites, mono zinc phosphate, mono calcium phosphate, sodium acid pyrophosphate, mono sodium phosphate, and the like, can be used. The acid or acid salt is selected so that it can be effectively combined with the filler to produce a synergistic effect and a balance of properties, such as flow and impact, in the polycarbonate or polycarbonate blend. In a further aspect, the weight ratio of acid to filler component, or acid:filler component weight ratio, can be from about 0.001 to about 0.04.

E. ARTICLES OF MANUFACTURE

In one aspect, the present invention pertains to shaped, formed, or molded articles comprising the disclosed PBMP monomers and thermoplastic compositions. The thermoplastic compositions can be molded into useful shaped articles by a variety of means such as injection molding, extrusion, rotational molding, blow molding and thermoforming to form articles. In one aspect, the article is made by a melt forming process selected from the group consisting of: injection molding, blow molding, sheet and film extrusion, profile extrusion, thermoforming, additive manufacturing, compression molding, fiber extrusion and powder sintering. In another aspect, the article may have a wall thickness of from 1.0 to 5.0 mm. In yet another aspect, the article can be transparent with a percent transmission above 70% or a percent haze below 10%, or a percent transmission above 70% and a percent haze below 10%. In some aspects, the article will be an article that is exposed to water or steam in its end use. In a further aspect, exposure can be continual immersion, or temporary exposure such as in washing either by hand or in a dishwasher or other device. In other aspects, the article will be exposed to steam in autoclaving such as for a medical or food service device. In further aspect, the article will be sterilized using steam or hot water. In still further aspects, the water exposure will be at a temperature above 40° C. In yet further aspects, the water temperature will be above 70° C.

The thermoplastic compositions described herein can also be made into film and sheet as well as components of laminate systems. In a further aspect, a method of manufacturing an article comprises melt blending the polycarbonate component, and any additional components; and molding the extruded composition into an article. In a still further aspect, the extruding is done with a twin-screw extruder.

In a further aspect, the article is molded. In a still further aspect, the article is extrusion molded. In yet a further aspect, the article is injection molded.

The compositions of the present invention are well suited for a variety of uses, including various articles of manufacture. For example, and without limitation, the compositions of the invention can be used for medical devices, food service uses, housewares, electronics, packaging, automotive parts, computer enclosures, trays, drinking glasses, pitchers, eye glasses, syringes, connectors, cell phone housings, keycaps, handles, bottles, sheets, films, coatings, and the like.

In some aspects, the article is selected from a medical device, surgical device, imaging device, monitoring device, blood care device, drug delivery device, interior trim, window, floor, cover, wall panel, door, enclosure, housing, panel, lighting switch, bedding part, furniture part, culinary device, food preparation device, food storage device, or food delivery device, or a combination thereof.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein can be different from the actual publication dates, which can require independent confirmation.

F. ASPECTS

In various aspects, the present invention pertains to and includes at least the following aspects: Aspect 1: An alkoxy polycarbonate comprising: a) repeating carbonate units derived from at least one ortho alkoxy bisphenol monomer; wherein the ortho alkoxy bisphenol monomer does not exhibit a half maximal inhibitory concentration ($IC_{50}$) less than 0.00025M for alpha or beta in vitro estradiol receptors; and b) wherein when the polycarbonate is subjected to conditions effective to provide at least one hydrolysis product, the at least one hydrolysis product does not exhibit a half maximal inhibitory concentration ($IC_{50}$) less than 0.00025M for alpha or beta in vitro estradiol receptors.

Aspect 2: The alkoxy polycarbonate of aspect 1, further comprising: a) a Mw in the range of from 3,000 to 80,000 Daltons; b) a phenolic end group content less than 20 meq/kg; c) a total chloride content less than 20 ppm; d) a transition metal content less than 20 ppm; and e) a residual phenolic monomer content less than 100 ppm.

Aspect 3: The alkoxy polycarbonate of aspects 1-2, wherein the ortho alkoxy bisphenol monomer has a structure represented by a formula:

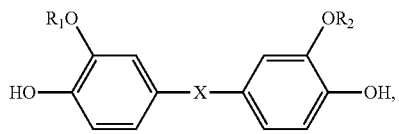

wherein each of R1 and R2 is independently selected from $C_1$-$C_{26}$ alkyl and $C_6$-$C_{26}$ alkaryl; wherein X is a bridging group connecting the two hydroxy-substituted aromatic groups selected from —O—, —S—, —S(O)—, —S(O)$_2$—, —C(O)—, or a $C_{3-18}$ organic group; and wherein the bridging group and the hydroxy substituent of each $C_6$ arylene group are disposed meta, or para to each other on the arylene group bearing the phenolic (OH) functionality.

Aspect 4: The alkoxy polycarbonate of aspect 3, wherein X is a substituted or unsubstituted C3-C18 cycloalkylidene; a C3-C25 alkylidene of the formula —C(Rc)(Rd)- wherein Rc and Rd are each independently hydrogen, C1-12 alkyl, C1-12 cycloalkyl, C7-C12 arylalkyl, C1-C12 heteroalkyl, or cyclic C7-C12 heteroarylalkyl; or a group of the formula —C(+Re)- wherein Re is a divalent C1-C12 hydrocarbon group.

Aspect 5: The alkoxy polycarbonate of aspects 3-4, wherein X is selected from ethylidene, isopropylidene, isobutylidene neopentylidene, cyclohexylidene, alkyl substituted cyclohexylidene, aryl, cyclopentadecylidene, cyclododecylidene, sulfo, oxo, and bicycloheptylidene.

Aspect 6: The alkoxy polycarbonate of aspects 3-5, wherein each of R1 and R2 is independently selected from methyl, ethylidene, propylidene, butylidene, benzyl, phenyl, C1 to C4 alkyl phenyl, and cyclohexylidene.

Aspect 7: The alkoxy polycarbonate of aspects 3-6, wherein each of R1 and R2 is methyl.

Aspect 8: The alkoxy polycarbonate of aspects 3-7, wherein the ortho alkoxy bisphenol monomer is 4,4'(2,2'-isopropylidene)-bis(ortho methoxy)phenol (PBMP).

Aspect 9: The alkoxy polycarbonate of aspects 1-8, wherein the ortho alkoxy bisphenol monomer is at least 1 wt % derived from bio-based material.

Aspect 10: The alkoxy polycarbonate of aspect 1-9, wherein the ortho alkoxy bisphenol monomer is at least 20 wt % derived from bio-based material.

Aspect 11: The alkoxy polycarbonate of aspects 1-10, wherein the ortho alkoxy bisphenol monomer is at least 30 wt % derived from bio-based material.

Aspect 12: The alkoxy polycarbonate of aspects 1-11, wherein the ortho alkoxy bisphenol monomer is at least 40 wt % derived from bio-based material.

Aspect 13: The alkoxy polycarbonate of aspects 1-12, wherein the ortho alkoxy bisphenol monomer is at least 50 wt % derived from bio-based material.

Aspect 14: The alkoxy polycarbonate of aspects 1-13, wherein the ortho alkoxy bisphenol monomer is at least 60 wt % derived from bio-based material.

Aspect 15: The alkoxy polycarbonate of aspects 1-14, wherein the ortho alkoxy bisphenol monomer is at least 70 wt % derived from bio-based material.

Aspect 16: The alkoxy polycarbonate of aspects 1-15, wherein the ortho alkoxy bisphenol monomer is at least 80 wt % derived from bio-based material.

Aspect 17: The alkoxy polycarbonate of aspects 1-16, wherein the ortho alkoxy bisphenol monomer is at least 90 wt % derived from bio-based material.

Aspect 18: The alkoxy polycarbonate of aspects 1-17, wherein the ortho alkoxy bisphenol monomer is at least 99 wt % derived from bio-based material.

Aspect 19: The alkoxy polycarbonate of aspects 9-18, wherein the bio-based material comprises at least one lignocellulosic material, plant material, bio-based oil, pyrolysis oil, biorefinery waste, or a combination thereof.

Aspect 20: The alkoxy polycarbonate of aspects 1-19, wherein the alkoxy polycarbonate is a co-polycarbonate comprising repeating carbonate units derived from the ortho alkoxy bisphenol monomer and at least one additional phenolic monomer; and wherein the additional phenolic monomer does not exhibit a half maximal inhibitory concentration ($IC_{50}$) less than 0.00025M for alpha or beta in vitro estradiol receptors.

Aspect 21: The alkoxy polycarbonate of aspect 20, wherein the additional phenolic monomer comprises a bisphenolic monomer, a mono phenolic monomer, or a combination thereof.

Aspect 22: The alkoxy polycarbonate of aspect 20, wherein the additional phenolic monomer comprises resorcinol, hydroquinone, methyl hydroquinone, t-butyl hydroquinone, di-t-butyl hydroquinones (DTBHQ), biphenols, tetramethyl bisphenol-A, spiro biindane bisphenols (SBIBP), bis-(hydroxy aryl)-N-aryl isoindolinones, hydrogenated bisphenol-A, 4,4'-(diphenylmethylene)diphenol, or a combination thereof.

Aspect 23: The alkoxy polycarbonate of aspect 1-19, wherein the alkoxy polycarbonate is a co-polycarbonate comprising repeating carbonate units derived from the ortho alkoxy bisphenol monomer and at least one diol monomer; and wherein the diol monomer does not exhibit a half maximal inhibitory concentration ($IC_{50}$) less than 0.00025M for alpha or beta in vitro estradiol receptors.

Aspect 24: The alkoxy polycarbonate of aspect 24, wherein the diol monomer comprises cyclohexanedimethanol, 2,2',4,4'-tetramethyl-1,3-cyclobutanediol, isosorbide, or a combination thereof.

Aspect 25: The alkoxy polycarbonate of aspects 1-19, wherein the alkoxy polycarbonate is a poly(ester carbonate) comprising repeating carbonate units derived from the ortho alkoxy bisphenol monomer and at least one dicarboxylic acid monomer; and wherein the dicarboxylic acid monomer does not exhibit a half maximal inhibitory concentration ($IC_{50}$) less than 0.00025M for alpha or beta in vitro estradiol receptors.

Aspect 26: The alkoxy polycarbonate of aspect 25, wherein the at least one dicarboxylic acid monomer comprises isophthalic acid, terephthalic acid, a C6 to C36 aliphatic dicarboxylic acids, furan dicarboxylic acids, naphthalene dicarboxylic acids, sebacic acid, or a combination thereof.

Aspect 27: The alkoxy polycarbonate of aspects 1-26, further comprising at least one additive; and wherein each of the at least one additive does not exhibit a half maximal inhibitory concentration ($IC_{50}$) less than 0.00025M for alpha or beta in vitro estradiol receptors.

Aspect 28: The alkoxy polycarbonate of aspect 27, wherein the at least one additive comprises a stabilizer, antioxidant, colorant, impact modifier, flame retardant, anti-drip additive, mold release additive, lubricant, plasticizer, mineral additive, reinforcement additive, or a combination thereof.

Aspect 29: The alkoxy polycarbonate of aspect 28, wherein the one or more additive comprises a phosphite and wherein when the phosphite is subjected to conditions effective to provide one or more phosphite hydrolysis product, each of the one or more phosphite hydrolysis products does not exhibit a half maximal inhibitory concentration ($IC_{50}$) less than 0.00025M for alpha or beta in vitro estradiol receptors.

Aspect 30: The alkoxy polycarbonate of aspect 29, wherein the phosphite comprises a diphenyl alkyl phosphite, phenyl dialkyl phosphite, trialkyl phosphite, dialkyl phosphite, triphenyl phosphite, diphenyl pentaerythritol diphosphite, or any combination thereof.

Aspect 31: The alkoxy polycarbonate of aspect 29, wherein the phosphite has a Mw greater than 200 Daltons.

Aspect 32: The alkoxy polycarbonate of aspects 1-31, wherein the alkoxy polycarbonate is end capped with aliphatic alcohols, phenol, phenyl chloroformate, guaiacol, ortho alkoxy phenols or mixture thereof.

Aspect 33: The alkoxy polycarbonate of aspects 1-32, further comprising at least one phosphorus compound and wherein when the alkoxy polycarbonate is subjected to conditions effective to provide at least one phosphorous compound hydrolysis product, each of the at least one phosphorous compound hydrolysis product does not exhibit a half maximal inhibitory concentration ($IC_{50}$) less than 0.00025M for alpha or beta in vitro estradiol receptors.

Aspect 34: The alkoxy polycarbonate of aspect 33, wherein the phosphorus compound comprises an aryl phosphate comprising triphenyl phosphate, resorcinol phenyl diphosphate, spirobiindane phenyl diphosphate, di-tertbutyl hydroquinone phenyl diphosphate, biphenol phenyl diphosphate, hydroquinone phenyl diphosphate, or a combination thereof.

Aspect 35: The alkoxy polycarbonate of aspects 1-34, wherein the alkoxy polycarbonate comprises less than about 100 ppm of bromide and less than about 100 ppm of chloride.

Aspect 36: The alkoxy polycarbonate of aspects 1-35, wherein the alkoxy polycarbonate comprises at least 20 wt % ortho alkoxy bisphenol monomer.

Aspect 37: The alkoxy polycarbonate of aspects 1-36, wherein the alkoxy polycarbonate comprises at least 30 wt % ortho alkoxy bisphenol monomer.

Aspect 38: The alkoxy polycarbonate of aspects 1-37, wherein the alkoxy polycarbonate comprises at least 40 wt % ortho alkoxy bisphenol monomer.

Aspect 39: The alkoxy polycarbonate of aspects 1-38, wherein the alkoxy polycarbonate comprises at least 50 wt % ortho alkoxy bisphenol monomer.

Aspect 40: The alkoxy polycarbonate of aspects 1-39, wherein the alkoxy polycarbonate exhibits a Tg of at least 120° C.

Aspect 41: The alkoxy polycarbonate of aspects 1-40, wherein the alkoxy polycarbonate exhibits a Tg of at least 130° C.

Aspect 42: The alkoxy polycarbonate of aspects 1-41, wherein the alkoxy polycarbonate exhibits a Tg in the range of from 120° C. to 300° C.

Aspect 43: A polymer blend comprising: a) a first polymer component comprising at least one alkoxy polycarbonate according to aspect 1-42; and b) a second polymer component.

Aspect 44: The polymer blend of aspect 43, wherein the second polymer component comprises one or more of at least one polyester, styrene acrylonitrile, acrylonitrile butadiene styrene, methyl methacrylate, methacrylate butadiene styrene, styrene maleic anhydride, styrene butadiene styrene, styrene ethylene butadiene styrene, polystyrene, polyolefin, polyetherimide, or a combination thereof.

Aspect 45: An article of manufacture comprising the alkoxy polycarbonate according to aspect 1.

Aspect 46: The article of aspect 45, wherein the article is made by a melt forming process selected from the group consisting of: injection molding, blow molding, sheet and film extrusion, profile extrusion, thermoforming, additive manufacturing, compression molding, fiber extrusion and powder sintering.

Aspect 47: The article of aspect 46, wherein the article has a wall thickness of from 1.0 to 5.0 mm, a percent transmission above 70% and a percent haze below 10%.

Aspect 48: The article of aspect 46, wherein the article is exposed to water or steam in its end use.

Aspect 49: A method for preparing a bisphenol monomer, the method comprising: a) providing a phenol having at least one alkoxy substituent ortho to the hydroxyl group; b) providing a ketone; and c) reacting the phenol and ketone under conditions effective to provide a reaction product comprising an ortho alkoxy bisphenol monomer; wherein the ortho alkoxy bisphenol monomer does not exhibit a half maximal inhibitory concentration ($IC_{50}$) less than 0.00025M for alpha or beta in vitro estradiol receptors.

Aspect 50: The method of aspect 49, wherein the phenol comprises guaiacol (2-methoxyphenol).

Aspect 51: The method of aspect 49-50, wherein the phenol is at least 1 wt % derived from bio-based material.

Aspect 52: The method of aspect 51, wherein the phenol is at least 20 wt % derived from bio-based material.

Aspect 53: The method of aspect 51, wherein the phenol is at least 30 wt % derived from bio-based material.

Aspect 54: The method of aspect 51, wherein the phenol is at least 40 wt % derived from bio-based material.

Aspect 55: The method of aspect 51, wherein the phenol is at least 50 wt % derived from bio-based material.

Aspect 56: The method of aspect 51, wherein the phenol is at least 60 wt % derived from bio-based material.

Aspect 57: The method of aspect 51, wherein the phenol is at least 70 wt % derived from bio-based material.

Aspect 58: The method of aspect 51, wherein the phenol is at least 80 wt % derived from bio-based material.

Aspect 59: The method of aspect 51, wherein the phenol is at least 90 wt % derived from bio-based material.

Aspect 60: The method of aspect 51, wherein the phenol is at least 99 wt % derived from bio-based material.

Aspect 61: The method of aspects 49-60, wherein the bio-based material comprises at least one lignocellulosic material, plant material, or a combination thereof.

Aspect 62: The method of aspects 49-61, wherein conditions effective comprise reacting the phenol and ketone in the presence of an acidic catalyst.

Aspect 63: The method of aspect 62, wherein the catalyst comprises $H_2SO_4$, an ion exchange resin catalyst, C1-C24 alkyl or alkyl aryl sulfonic acid, HCl, or a combination thereof.

Aspect 64: The method of aspect 63, wherein the catalyst is HCl.

Aspect 65: The method of aspects 49-64, wherein the conditions effective to provide comprise reacting the phenol and ketone in the presence of a mercapto carboxylic acid.

Aspect 66: The method of aspects 49-65, wherein the conditions effective to provide comprise adjusting the temperature to at least about 55° C.

Aspect 67: The method of aspects 49-66, wherein the conditions effective to provide comprise maintaining the reaction for at least about 2 hours.

Aspect 68: The method of aspects 49-67, wherein the phenol and ketone are provided at a molar ratio of at least about 2:1.

Aspect 69: The method of aspects 49-68, wherein the phenol and ketone are provided at a molar ratio of at least about 3:1.

Aspect 70: The method of aspects 49-69, wherein the phenol and ketone are provided at a molar ratio of at least about 4:1.

Aspect 71: The method of aspects 49-70, wherein the phenol and ketone are provided at a molar ratio of at least about 5:1.

Aspect 72: The method of aspects 49-71, wherein the phenol and ketone are provided at a molar ratio of at least about 6:1.

Aspect 73: The method of aspects 49-67, wherein the phenol and ketone are provided at a molar ratio in the range of from at least about 2:1 to about 20:1.

Aspect 74: The method of aspects 49-73, wherein the ortho alkoxy bisphenol monomer has a structure represented by a formula:

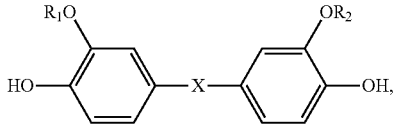

wherein each of R1 and R2 is independently selected from $C_1$-$C_{26}$ alkyl and $C_6$-$C_{26}$ alkaryl; wherein X is a bridging group connecting the two hydroxy-substituted aromatic groups selected from —O—, —S—, —S(O)—, —S(O)$_2$—, —C(O)—, or a $C_{3-18}$ organic group; and wherein the bridging group and the hydroxy substituent of each $C_6$ arylene group are disposed meta, or para to each other on the arylene group bearing the phenolic (OH) functionality.

Aspect 75: The method of aspect 74, wherein X is a substituted or unsubstituted C3-C18 cycloalkylidene; a C3-C25 alkylidene of the formula —C(Rc)(Rd)- wherein Rc and Rd are each independently hydrogen, C1-C12 alkyl, C1-C12 cycloalkyl, C7-12 arylalkyl, C1-C12 heteroalkyl, or cyclic C7-C12 heteroarylalkyl; or a group of the formula —C(=Re)- wherein Re is a divalent C1-C12 hydrocarbon group.

Aspect 76: The method of aspect 74, wherein X is selected from ethylidene, isopropylidene, isobutylidene neopentylidene, cyclohexylidene, alkyl substituted cyclohexylidene, aryl, cyclopentadecylidene, cyclododecylidene, sulfo, oxo, and bicycloheptylidene.

Aspect 77: The method of aspect 74, wherein each of R1 and R2 is independently selected from methyl, ethylidene, propylidene, butylidene, benzyl, phenyl, C1 to C4 alkyl phenyl, and cyclohexylidene.

Aspect 78: The method of aspect 74, wherein each of R1 and R2 is methyl.

Aspect 79: The method of aspects 49-78, wherein the ketone comprises a C3-C26 ketone.

Aspect 80: The method of aspects 49-79, wherein the ketone comprises a C6-C12 cyclic ketone.

Aspect 81: The method of aspects 49-80, wherein the ketone is acetone.

Aspect 82: The method of aspects 49-81, wherein the reaction product comprises at least about 50 wt % of the ortho alkoxy bisphenol monomer.

Aspect 83: The method of aspects 49-82, wherein the reaction product is a precursor for a polymerization reaction.

Aspect 84: The method of aspects 49-83, wherein the reaction product is 4,4'(2,2'-isopropylidene)-bis(ortho methoxy) phenol (PBMP).

Aspect 85: A method for preparing a bisphenol monomer, the method comprising: a) providing guaiacol; b) providing acetone with less than 1% aldehyde impurity present; and c) reacting the guaiacol and acetone in the presence of a catalyst under conditions effective to provide a reaction product comprising 4,4'(2,2'-isopropylidene)-bis(ortho methoxy)phenol (PBMP); wherein the PBMP does not exhibit a half maximal inhibitory concentration ($IC_{50}$) less than 0.00025M for alpha or beta in vitro estradiol receptors.

Aspect 86: A method for preparing an alkoxy polycarbonate, the method comprising: a) providing the bisphenol monomer of aspects 49-84; b) providing a carbonyl source reactant; and c) reacting the bisphenol monomer and carbonyl source reactant under conditions effective to provide a polycondensation reaction product comprising an alkoxy polycarbonate; wherein when the alkoxy polycarbonate provided in step f) is subjected to conditions effective to provide at least one hydrolysis product, each of the at least one hydrolysis products does not exhibit a half maximal inhibitory concentration ($IC_{50}$) less than 0.00025M for alpha or beta in vitro estradiol receptors.

Aspect 87: The method of aspect 86, wherein the bisphenol monomer is 4,4'(2,2'-isoPropylidene)-Bis(ortho Methoxy) Phenol (PBMP).

Aspect 88: The method of aspects 86-87, wherein the carbonyl source reactant comprises a carbonyl halide or a diaryl carbonate.

Aspect 89: The method of aspect 88, wherein the diaryl carbonate is diphenyl carbonate.

Aspect 90: The method of aspects 86-89, wherein the conditions effective comprise reacting the bisphenol monomer and carbonyl source reactant in the presence of a polycondensation catalyst.

Aspect 91: The method of aspects 86-90, wherein the conditions effective to provide a polycondensation reaction product comprise reacting the phenolic monomer and carbonyl source reactant in the presence of an end capping agent.

Aspect 92: The method of aspect 91, wherein the end capping agent comprises phenol, phenyl chloroformate, or guaiacol (2-methoxyphenol), or a combination thereof.

Aspect 93: The method of aspects 86-92, wherein after step c) the alkoxy polycarbonate is blended with at least one additive and wherein each of the at least one additive does not exhibit a half maximal inhibitory concentration ($IC_{50}$) less than 0.00025M for alpha or beta in vitro estradiol receptors.

Aspect 94: The method of aspects 86-93, further comprising providing at least one additional phenolic monomer wherein the additional phenolic monomer does not exhibit a half maximal inhibitory concentration ($IC_{50}$) less than 0.00025M for alpha or beta in vitro estradiol receptors; and wherein step c) comprises reacting the additional phenolic monomer, the bisphenol monomer, and the carbonyl source reactant in the presence of a catalyst under conditions effective to provide a polycondensation reaction product comprising a co-alkoxy polycarbonate.

Aspect 95: The method of aspect 94, wherein the additional phenolic monomer comprises resorcinol, hydroquinone, methyl hydroquinone, t-butyl hydroquinone, di-t-butyl hydroquinones (DTBHQ), biphenols, tetramethyl bisphenol-A, spiro biindane bisphenols (SBIBP), bis-(hydroxy aryl)-N-aryl isoindolinones, hydrogenated bisphenol-A, 4,4'-(diphenylmethylene)diphenol, or a combination thereof.

Aspect 96: The method of aspects 86-95, further comprising providing at least one diol monomers wherein each of the diol monomers does not exhibit a half maximal inhibitory concentration ($IC_{50}$) less than 0.00025M for alpha or beta in vitro estradiol receptors; and wherein step c) comprises reacting the diol monomers, the bisphenol monomer, and the carbonyl source reactant in the presence of a catalyst under conditions effective to provide a polycondensation reaction product comprising a co-alkoxy polycarbonate.

Aspect 97: The method of aspect of 96, wherein the diol monomer comprises cyclohexanedimethanol, 2,2',4,4'-tetramethyl-1,3-cyclobutanediol, isosorbide, or a combination thereof.

Aspect 98: The method of aspects 86-97, further comprising the step of providing at least one dicarboxylic acid or phenolic carboxylic acid monomers wherein each of the dicarboxylic acid or phenolic carboxylic acid monomers does not exhibit a half maximal inhibitory concentration ($IC_{50}$) less than 0.00025M for alpha or beta in vitro estradiol receptors; and wherein step c) comprises reacting the dicarboxylic acid or phenolic carboxylic acid monomers, the bisphenol monomer, and the carbonyl source reactant in the presence of a catalyst under conditions effective to provide a polycondensation reaction product comprising a co-alkoxy polycarbonate.

Aspect 99: The method of aspects 86-98, wherein the alkoxy polycarbonate exhibits a Tg of at least 120° C.

Aspect 100: The method of aspects 86-99, wherein the alkoxy polycarbonate exhibits a Tg of at least 130° C.

Aspect 101: The method of aspects 86-100, wherein the alkoxy polycarbonate exhibits a Tg of at least 140° C.

Aspect 102: The method of aspect 98, wherein the dicarboxylic acid monomer comprises isophthalic acid, terephthalic acid, a $C_6$ to $C_{36}$ aliphatic dicarboxylic acids, furan dicarboxylic acids, naphthalene dicarboxylic acids, sebacic acid, or a combination thereof.

G. EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric. Unless indicated otherwise, percentages referring to composition are in terms of wt %.

There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable experimentation will be required to optimize such process conditions.

General Methods

All materials and reagents were used as received from the supplier unless otherwise indicated.

HPLC was performed using Agilent 1100 Series auto injector instrument having PDA detector, water-acetonitrile as mobile phase, and measured at 240 nm.

$^1$H and $^{13}$C NMR analyses were performed using Bruker 300 MHz instrument to record Nuclear Magnetic Resonance (NMR) spectral measurements with a solution of monomer or polymer in deuterated chloroform ($CDCl_3$) or mixture of deuterated dimethyl sulfoxide (DMSO-d6).

Synthesis of PBMP

Example 1

3 eq. Guaiacol was reacted with 1 eq. of acetone in presence of 10 wt % of concentrated $H_2SO_4$ (relative to the total amount of phenol and ketone) and 600-1300 ppm (based on total reactant content) of 3-mercaptopropionic acid (3-MPA) at 80° C. for 5-6 hours, yielding a mixture of PBMP, cyclic, and isomeric products (Ratio 50:10:40).

Example 2

3 eq Guaiacol was reacted with 1 eq of acetone in presence of 5 wt % of an ion exchange resin (IER) catalyst (relative to the total amount of phenol and ketone) and 600-1300 ppm (based on total reactant content) of 3-mercaptopropionic acid (3-MPA) at 80° C. for 5-12 hours, yielding a mixture of PBMP, cyclic, isomeric products, and starting materials (Ratio 10:5:5:80).

Example 3

3 eq. Guaiacol was reacted with 1 eq. of acetone in presence of 0.3 wt % of dodecyl benzene sulfonic acid (DBSA) catalyst (relative to the total amount of phenol and ketone) and 600-1300 ppm (based on total reactant content) of 3-mercaptopropionic acid (3-MPA) at 80° C. for 12 hours, yielding a mixture of PBMP, cyclic, isomeric products, and starting materials (Ratio 10:5:5:80).

Example 4

Figure 2:
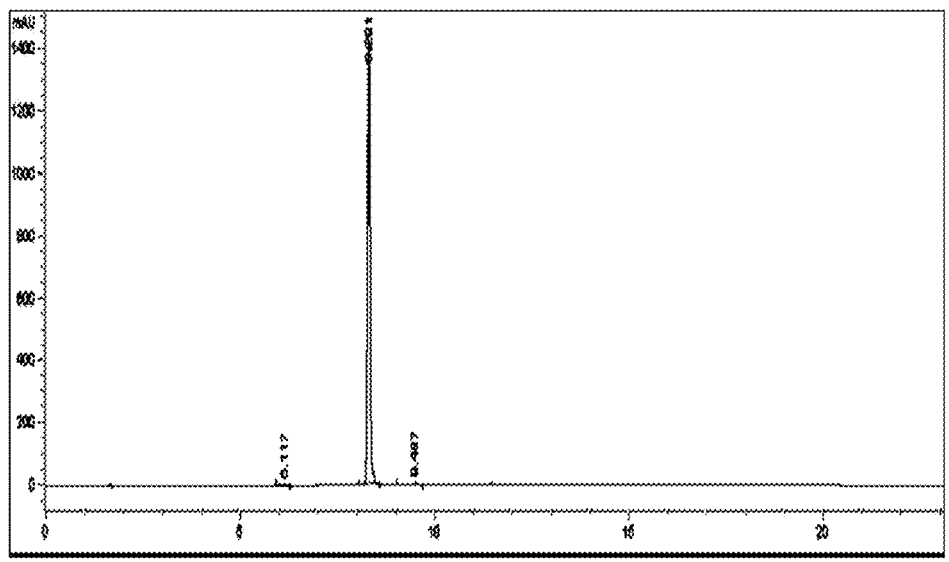
FIG. 2 shows representative HPLC data of PBMP monomer prepared according to the present invention.

6 eq. Guaiacol was reacted with 1 eq. of acetone in presence of 30 wt % concentrated HCl ((relative to the total amount of phenol and ketone) and 600-1300 ppm (based on total reactant content) of 3-Mercaptopropionic acid (3-MPA)

at 90° C. for 5-6 hours, yielding a mixture of PBMP and isomeric products (95:5). The crude product was then treated with aqueous 10 wt % NaOH solution (e.g., pH 12-14) for 30 min to convert PBMP to its sodium salt. The formed sodium salt of PBMP was then filtered, washed with organic solvent to remove residual guaiacol and other impurities. The sodium salt of PBMP was dissolved in deionized water and the pH was adjusted to 2-3 using dilute HCl, followed by subsequent extraction with ethyl acetate and evaporation of ethylacetate layer, to obtain highly pure PBMP (>99%), substantially free of isomeric and cyclic products. The product formation was confirmed by proton NMR (FIG. 1) and purity by HPLC (FIG. 2).

Biological Testing

Estradiol binding activity of various compounds and potential polymer hydrolysis or thermolysis products were tested using a conventional in vitro competitive binding assay, and quantified by the half maximal inhibitory concentration ($IC_{50}$) value. In one aspect, PBMP according to the present invention is capable for use as component starting materials in the manufacture of alkoxy polycarbonate compositions. In a further aspect, component starting materials can mimic or replicate various chemical species that can be produced under certain conditions, for example high pH (8 to 12) or low pH (1 to 6), as hydrolytic degradation products derived from alkoxy polycarbonates comprising the component starting materials. The ($IC_{50}$) binding concentrations for the alpha ($\alpha$) and/or beta 1 ($\beta 1$) in vitro estradiol receptors were tested. Tests were conducted by displacement of radiolabeled 17b-estradiol.

The compound to be evaluated, for example guaiacol bisphenol, was tested as to its binding affinity for recombinant human estradiol receptors (rhER) alpha ($\alpha$) and/or beta 1 ($\beta 1$) in vitro. 17$\beta$-estradiol ($E_2$) was used a standard whose relative binding affinity was defined as 100%. Competitive binding assays were performed by incubating rhER alpha ($\alpha$) and/or beta 1 ($\beta 1$) with 10 nM [$^3$H]estradiol (the radio ligand) in the presence or absence of increasing concentrations, 0.25 to 250,000 nM, of the PBMP test compounds (nM is nano molar). Each data point is the average of at least two assays. Compounds were diluted 10 fold in binding buffer and then 1:4 in the final assay mix. The final concentration of ethanol or DMSO in the assay well was 5%. The highest concentration of the PBMP was 2.5×E-4 M (250,000 nM). The compound under evaluation was tested at seven concentrations over log increments. The lowest concentration was 2.5×E-10 M (0.25 nM). The $IC_{50}$ is the concentration of test compound at which about 50% of the radio labeled estradiol was displaced from the estradiol receptor.

The experimental ($IC_{50}$) values are provided in the Table 1 below. As shown, many mono and bisphenols (EX. A-F) show an undesired high level of receptor binding. However, surprisingly, preferred phenolic compounds (EX. 1-2) utilized in the alkoxy polycarbonate compositions of the invention either did not show any detectable estradiol binding in these tests or, at a minimum, did not exhibit an ($IC_{50}$) binding concentrations less than 2.5×E-4 M. An entry of >2.5×E-4 for compounds in Table 1 indicates that those compounds did not compete to the extent of 50% with radio labeled 17B-estradiol at the highest concentration (250,000 nM) tested. That is there was no estradiol displacement and hence no $IC_{50}$ could be determined, the $IC_{50}$, if there is displacement at all, is some value greater than 2.5×E-4.

TABLE 1

| Ex. | Compounds | $IC_{50}$ rhER ($\alpha$) | $IC_{50}$ rhER ($\beta 1$) |
|---|---|---|---|
| A | 17b-estradiol control | 1.0 × E−9 | 8.2 × E−9 |
| B | p-Cumyl Phenol (CAS# 599-64-4) | 1.4 × E−4 | 9.8 × E−6 |
| C | Dihydroxy Diphenyl Ether (CAS# 1965-09-9) | 6.0 × E−5 | 1.4 × E−5 |
| D | Bisphenol Acetophenone (CAS# 1571-75-1) | 1.2 × E−5 | 1.4 × E−6 |
| E | Dimethyl Acetophenone Bisphenol (CAS# 4754-63-6) | 4.8 × E−6 | 3.5 × E−6 |
| F | Diphenolic Acid Methyl Ester (CAS# 7297-85-0) | 1.9 × E−5 | 1.1 × E−5 |
| 1 | 4,4' (2,2'-isoPropylidene)-Bis(ortho Methoxy)Phenol (PBMP) | >2.5 × E−4 | >2.5 × E−4 |
| 2 | Phenol (CAS# 108-95-2) | >2.5 × E−4 | >2.5 × E−4 |

Figure 3:
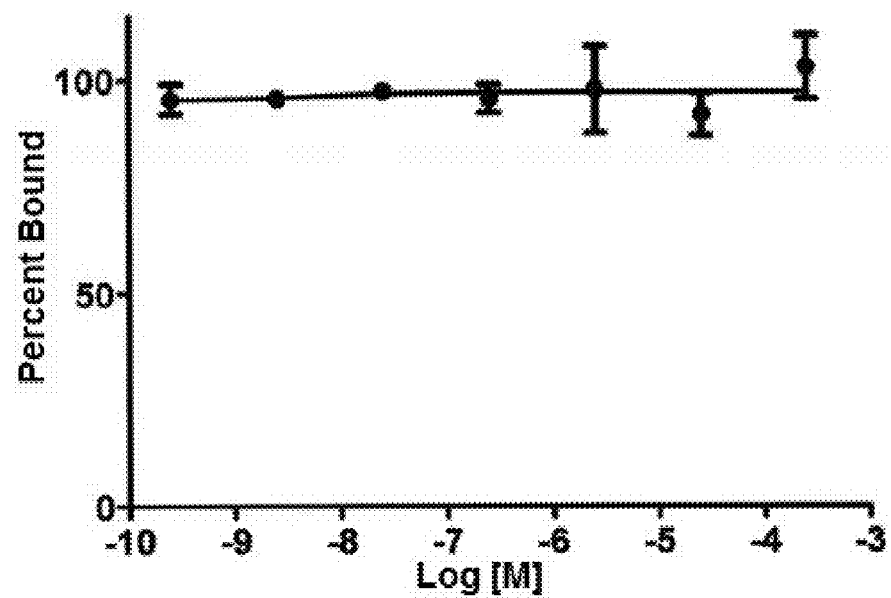
FIG. 3 shows representative ER-alpha binding data of PBMP monomer prepared according to the present invention.
Figure 4:
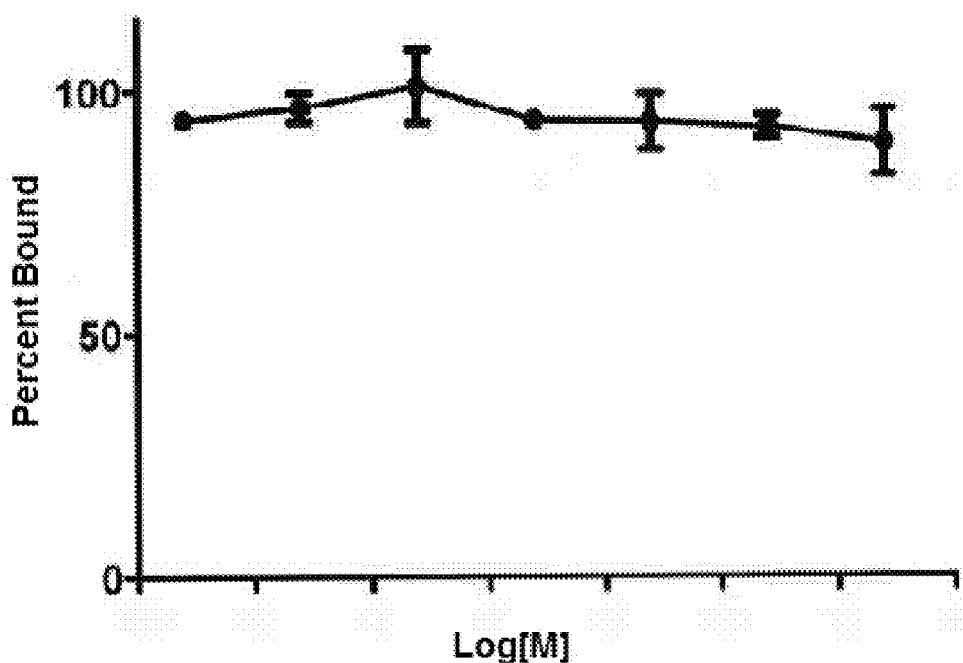
FIG. 4 shows representative ER-beta binding data of PBMP monomer prepared according to the present invention.

$IC_{50}$ is the conc. of the candidate that displaces 50% of the radioactive ligand from the rhER cells
>2.5 × E4 compounds did not compete to the extent of 50% with radiolabeled 17B-estradiol at the highest conc. (250,000 nM) tested, no $IC_{50}$ can be determined As shown in FIGS. 3 ($IC_{50}$ rhER ($\alpha$)=alpha receptor binding) and 4 ($IC_{50}$ rhER ($\beta 1$=beta receptor binding), the PBMP monomer shows no estradiol binding activity, even at the highest concentration. That is, even at a concentration of 2.5×E-4 M, there was no displacement of estradiol. The PBMP monomer utilized to prepare the alkoxy polycarbonate compositions of the invention either did not show any detectable estradiol binding in these tests or, at a minimum, did not exhibit an ($IC_{50}$) binding concentrations less than 2.5×E-4 M. Without wishing to be bound by a particular theory, it is believed that when polycarbonate produced from PBMP monomers of the present invention is subjected to conditions effective to provide one or more degradation products, such as a hydrolysis or thermolysis product, each of the one or more degradation products does not displace estradiol even at a concentrations as high as 0.00025 M. In further aspects, when the polycarbonate produced from PBMP monomers is subjected to conditions effective to provide one or more degradation products, each of the one or more degradation products also does not exhibit a half maximal inhibitory concentration ($IC_{50}$) equal to or greater than 0.00025 M for alpha or beta in vitro estradiol receptors.

Synthesis and Characterization of PBMP Polycarbonate

Example 5

Figure 5A:
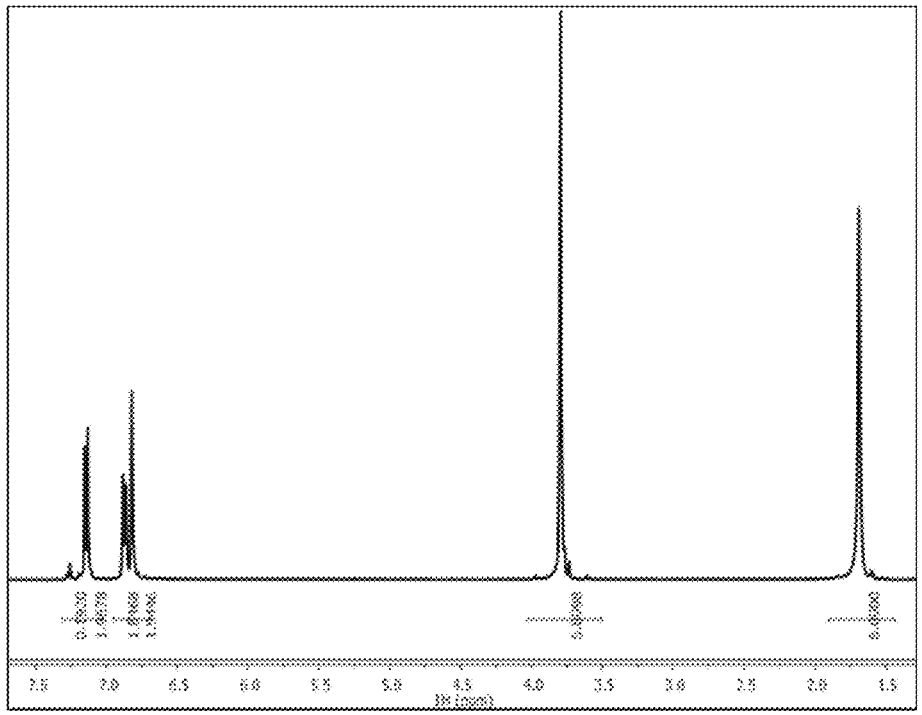
FIGS. 5A and 5B show a representative $^1$H NMR spectrum of a PBMP polycarbonate prepared according to the present invention.
Figure 5B:
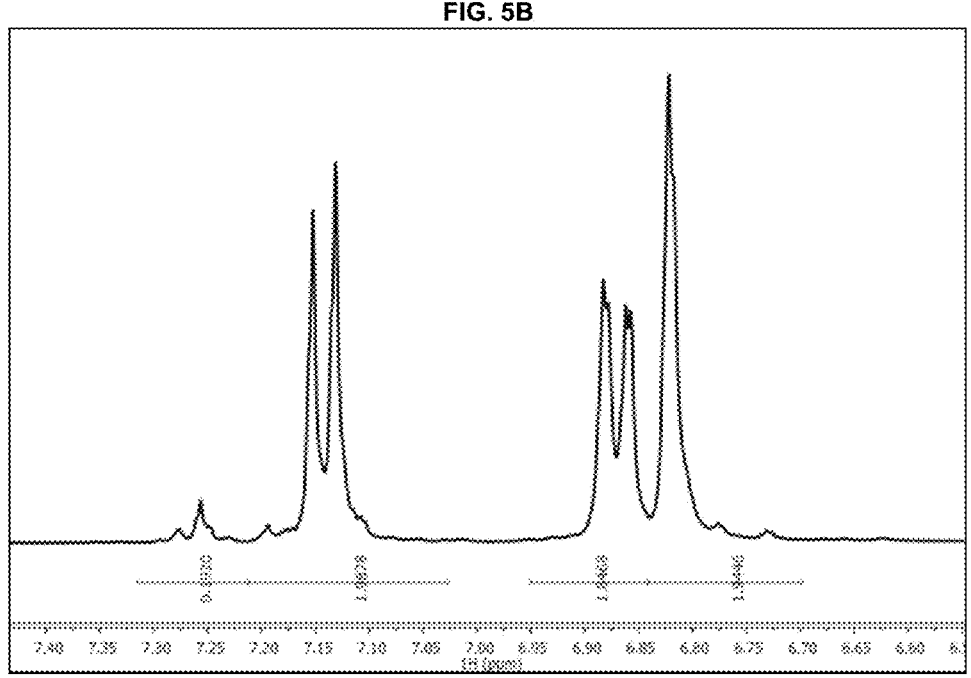
Figure 6:
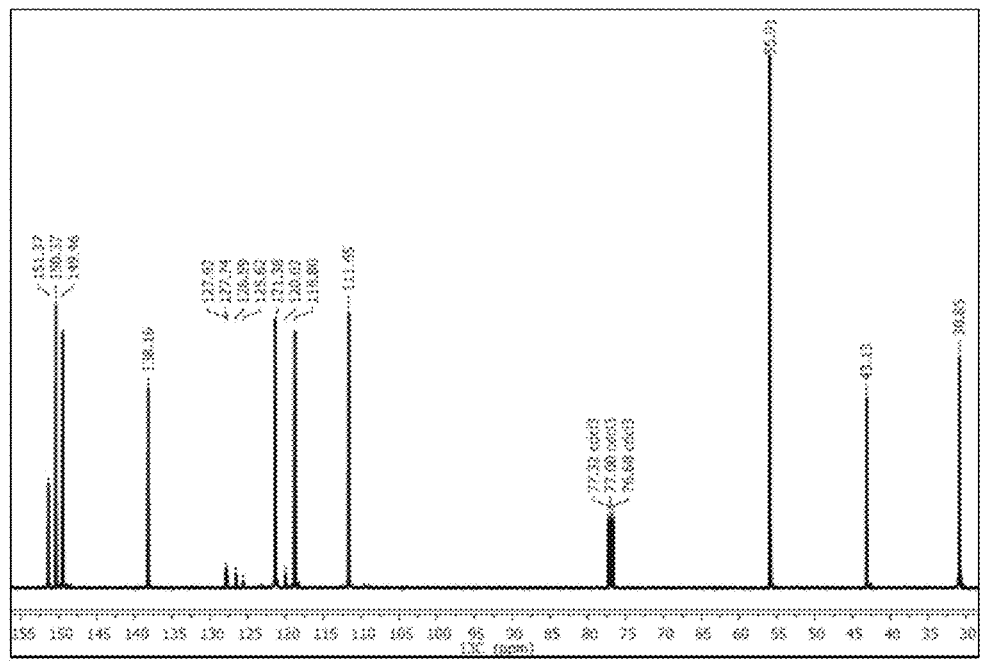
FIG. 6 shows a representative $^{13}$C NMR spectrum of a PBMP polycarbonate prepared according to the present invention.
Figure 7:
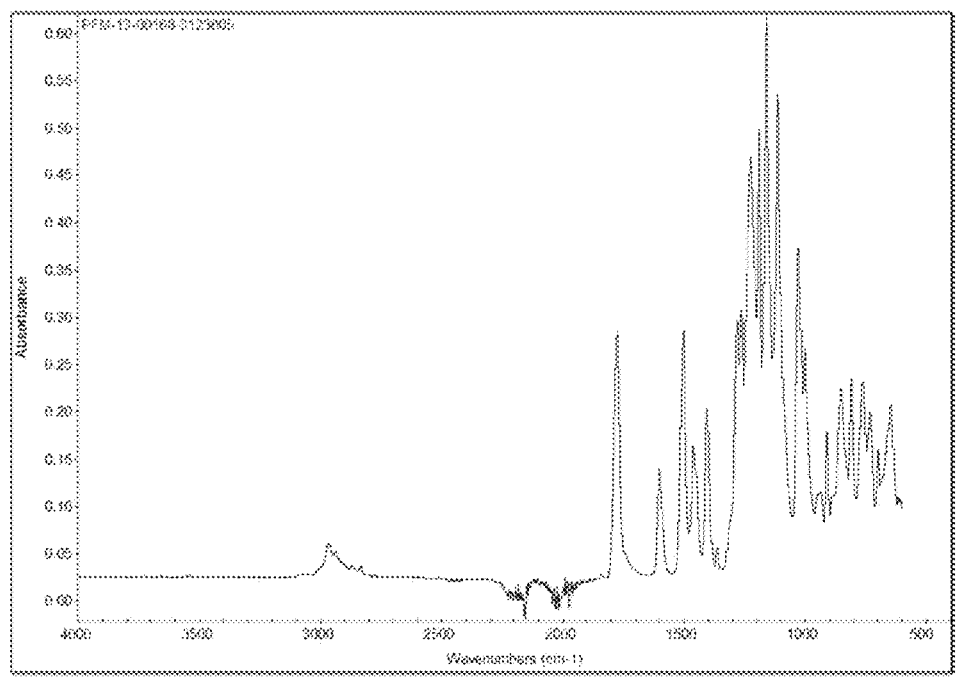
FIG. 7 shows representative IR absorbance spectrum for a PBMP polycarbonate prepared according to the present invention.
Figure 8:
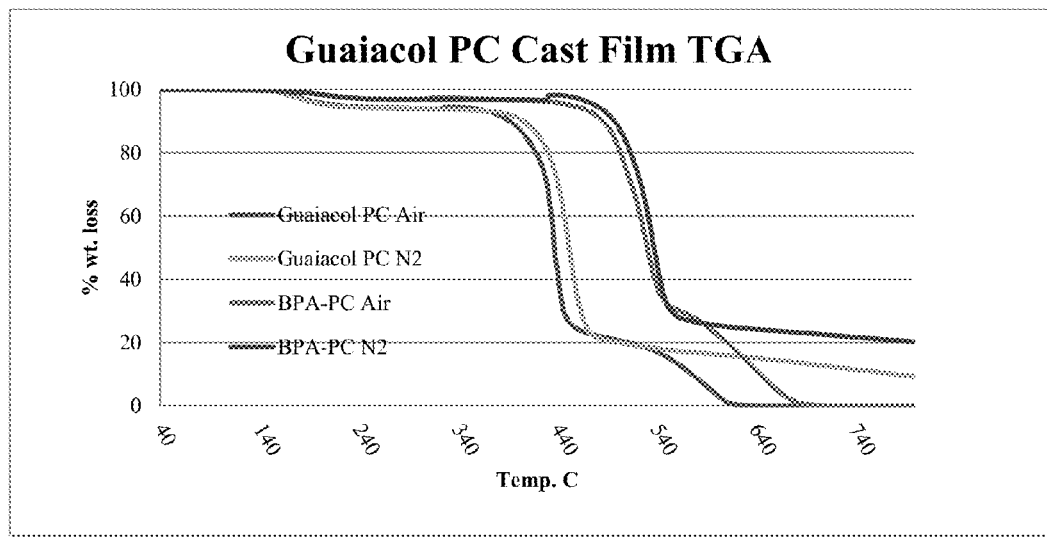
FIG. 8 shows representative thermogravimetric analysis (TGA) data for a PBMP polycarbonate prepared according to the present invention and BPA polycarbonate.

A polycarbonate comprising PBMP monomers of the present invention was prepared following an interfacial polycarbonate synthesis. To a 2 L flask equipped with mechanical agitation, condenser, and a caustic vent scrubber, was charged $CH_2Cl_2$ (500 ml), deionized water (300 ml) and 4,4'(2-isopropylidene)bis[2-methoxyphenol (20.0 g, 0.069 moles, CAS#64170-83-8), Mixing was started and phosgene (10 g, 0.10 moles) was added subsurface at a rate of 1.0 g/minutes while a 33 wt % solution of sodium hydroxide was added at a rate to maintain pH 7. After phosgene addition was complete, additional 33 wt % sodium hydroxide solution was added to reach pH=9 to 10 and the batch was purged with nitrogen for 10 minutes. p-Cumylphenol (0.37 g, 0.0017 mol) was added and the reaction mixture stirred for 10 minutes. Triethylamine (TEA) catalyst (0.29 ml) was then added and the batch stirred for an additional 10 minutes. Additional phosgene (4 g, 0.04 mole) was added subsurface at a rate of 1 g/min while 33 wt % sodium hydroxide was added to maintain pH=9. The batch was purged with nitrogen for 10 minutes. Stirring was stopped and the batch allowed to phase separate. The organic phase containing polymer was separated, washed with 1N HCl (1×500 ml) and then with deionized water (3×500 ml). The polymer solution was then slowly fed into approximately 2 L of hot water with rapid stirring to boil off the $CH_2Cl_2$, and the resulting white polymer powder was isolated by filtration and dried in air at 60° C. overnight. The PBMP polycarbonate polymer had a dry chloride content of 21 ppm. GPC of the polymer powder Mw=23,393 and Mn=6,600 vs. PC standard. Glass transition temperature (Tg) as measured by DSC was 126° C. Tg was determined by differential scanning calorimetry (DSC) with a 20° C./min. heating rate and recoded on second heat in accordance with ASTM D7426. The Tg of over 120° C. indicates that the PBMP-PC polymer will have good practical use in many applications, for example, involving exposure to boiling water or autoclave sterilization. One gram of the dry polymer powder was extracted with approximately 10 ml. acetonitrile ($CH_3CN$) and analyzed by liquid chromatography. The polymer had less than 100 ppm residual 4,4'-(2-isopropylidene)bis[2-methoxyphenol] (G-bisphenol) monomer. $^1$H-NMR analysis was carried out on the resulting PBMP polycarbonate polymer and the data are shown in FIG. 8. $CDCl_3$ was used as solvent. Chemical shifts are consistent with the expected PBMP polycarbonate structure (FIGS. 5A & 5B). $^{13}$C-NMR analysis was carried out on the resulting PBMP alkoxy bisphenol acetone polycarbonate polymer in $CDCl_3$ solution the data are shown in FIG. 6. Chemical shifts are consistent with the expected PBMP polycarbonate structure Infra-red (IR) spectrum of a solution of the polycarbonate is shown in FIG. 7 and is also consistent with the alkoxy bisphenol acetone polycarbonate structure.

The PBMP polycarbonate was used to prepare cast films by dissolving approximately 3 gm. of PBMP-PC in 30 ml methylene chloride. Solvent was evaporated overnight at room temperature and films were dried for 3 hr. at approximately 80° C.

A cast film sample was analyzed by GPC ($CH_2Cl_2$, calibrated against BPA PC standards) which showed weight average molecular weight Mw=23111.

Properties and Testing of PBMP Polycarbonate

Thermal gravimetric analysis (TGA) was done under nitrogen or air from 40 to 800° C. at a rate of 20° C./min. PBMP-PC (Guaiacol-PC) and standard BPA-PC samples were tested to determine the onset and maximum weight loss under nitrogen and air by thermo gravimetric analysis (TGA). TGA data for the samples tested are shown in Table 2 and FIG. 8. The samples show an early loss of weight under 175° C. likely due to residual solvent from the film casting. The max rate of wt. loss for the guaiacol PC, while not as high as BPA-PC, is still above 430° C. The 10% wt. loss does not occur until over 400° C.

TABLE 2

| Guaiacol-PC | BPA-PC |
| --- | --- |
| 6% wt loss 158° C. | 3% wt loss 175° C. |
| 10% wt. loss 406° C. | 10% wt. loss 490° C. |
| max wt. loss 436° C. | max wt. loss 530° C. |
| 79% wt. loss 500° C. | 70% wt. loss 570° C. |
| 91% total wt loss $N_2$ | 80% total wt loss $N_2$ |

The PBMP-PC alkoxy polycarbonate shows high heat capability with a glass transition temperature (Tg) of 126° C., and thermal stability was shown by less than 10% TGA weight loss below 390° C. in either air or nitrogen.

Figure 9:
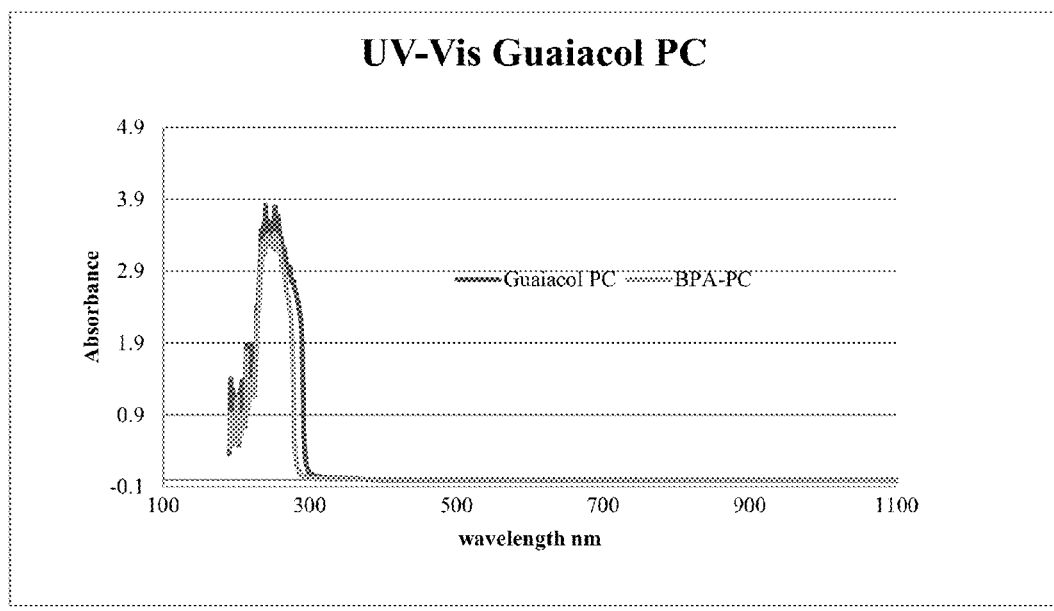
FIG. 9 shows representative UV-Visible light absorbance spectrum for a PBMP polycarbonate prepared according to the present invention and BPA polycarbonate.

Ultraviolet-visible spectroscopy (UV-Vis) spectroscopy analysis was carried out on the PBMP polycarbonate polymer (FIG. 9) and a standard BPA polycarbonate polymer (FIG. 7). The IR spectra data for both samples are shown in Table 3 and FIG. 9. Spectra were taken in solution of 0.1 g polymer in 50 ml methylene chloride. The data show both samples exhibit very similar absorption in the visible range. Cast PBMP-PC film showed a high transparency (>80% T), low color (Yellowness Index <10) and low haze (<5% H).

TABLE 3

| Absorbance | PBMP-PC | BPA-PC | Shift (nm) |
| --- | --- | --- | --- |
| 0.05 | 292 | 308 | 16 |
| 0.1 | 299 | 285 | 14 |
| 0.5 | 293 | 279 | 14 |
| 1.0 | 291 | 277 | 14 |
| peak | 252 | 243/252 | — |

Hydrolytic stability was performed by subjecting samples to hydrolytic stress by exposing the cast films to approximately 110° C. steam for 0-11 days. Steam was generated from deionized water with no additives. Hydrolytic stability was assessed for PBMP-PC, standard BPA-PC, BPA-PC with 0.03% tris (2,4 di-t-butyl phenyl) phosphite samples by comparison of the weight average molecular weight ("Mw") of polycarbonate polymer before and after hydrolytic stress as described above. The data were converted to percent retention of the initial Mw and the data are shown in Table 4. The PBMP-PC (Guaiacol-PC) showed good retention of molecular weight (Mw) on exposure to steam showing only a moderate rate of hydrolysis with 79% Mw retention after 11 days and retention of film integrity.

Mn and Mw were determined using data obtained by standard chromatographic procedures. Briefly, GPC was carried out by first dissolving the sample at 1 mg/ml concentration in dichloromethane. The sample was then analyzed by GPC using a Polymer Laboratories MiniMIX C column (Polymer Laboratories, a division of Varian, Inc, Amherst, Mass.) with a mobile phase of dichloromethane and a flow rate of 0.3 ml/min. Detection wavelength was 254 nm. Mw results were reported against polycarbonate standards.

TABLE 4

| | Day | PC Cast Film | PBMP PC | PC w/ phosphite |
| --- | --- | --- | --- | --- |
| Molecular | 0 | 30496 | 23111 | 29081 |
| Weight | 2 | 29662 | 22205 | 26268 |
| (Mw) | 4 | 28178 | 21149 | 23487 |
| | 8 | 26667 | 19328 | 14594 |
| | 11 | 25840 | 18314 | 11166 |
| % Mw | 0 | 100 | 100 | 100 |
| Retention | 2 | 97.1 | 96.1 | 90.3 |
| (Mw) | 4 | 92.3 | 91.5 | 80.8 |
| | 8 | 87.4 | 83.6 | 50.2 |
| | 11 | 84.7 | 79.2 | 38.4 |

The PBMP-PC shows good clarity, low color, practical heat resistance (126° C. Tg), resistance to hydrolysis under exposure to steam with a composition that does not exhibit a half maximal inhibitory concentration ($IC_{50}$) less than 0.00025M for alpha or beta in vitro estradiol receptors;

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

The patentable scope of the invention is defined by the claims, and can include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An alkoxy polycarbonate comprising:
   repeating carbonate units derived from at least one ortho alkoxy bisphenol monomer; wherein the ortho alkoxy bisphenol monomer does not exhibit a half maximal inhibitory concentration ($IC_{50}$) less than 0.00025M for alpha or beta in vitro estradiol receptors; and
   wherein when the alkoxy polycarbonate is subjected to conditions effective to provide at least one hydrolysis product, the at least one hydrolysis product does not exhibit a half maximal inhibitory concentration ($IC_{50}$) less than 0.00025M for alpha or beta in vitro estradiol receptors; and
   wherein the alkoxy polycarbonate comprises:
   a) a Mw in the range of from 3,000 to 80,000 Daltons;
   b) a phenolic end group content less than 20 meq/kg;
   c) a total chloride content less than 20 ppm;
   d) a transition metal content less than 20 ppm; and
   e) a residual phenolic monomer content less than 100 ppm.

2. The alkoxy polycarbonate of claim 1, wherein the ortho alkoxy bisphenol monomer has a structure represented by a formula:

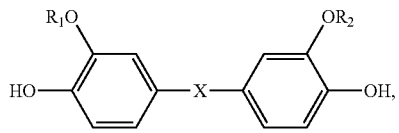

wherein each of R1 and R2 is independently selected from $C_1$-$C_{26}$ alkyl and $C_6$-$C_{26}$ alkaryl; wherein X is a bridging group connecting the two hydroxy-substituted aromatic groups selected from —O—, —S—, —S(O)—, —S(O)$_2$—, —C(O)—, or a $C_{3-18}$ organic group; and wherein the bridging group and the hydroxy substituent of each $C_6$ arylene group are disposed meta, or para to each other on the arylene group bearing the phenolic (OH) functionality.

3. The alkoxy polycarbonate of claim 2, wherein X is selected from ethylidene, isopropylidene, isobutylidene neopentylidene, cyclohexylidene, alkyl substituted cyclohexylidene, aryl, cyclopentadecylidene, cyclododecylidene, sulfo, oxo, and bicycloheptylidene; and wherein each of R1 and R2 is independently selected from methyl, ethylidene, propylidene, butylidene, benzyl, phenyl, C1 to C4 alkyl phenyl, and cyclohexylidene.

4. The alkoxy polycarbonate of claim 2, wherein each of R1 and R2 is methyl.

5. The alkoxy polycarbonate of claim 2, wherein the ortho alkoxy bisphenol monomer is 4,4'(2,2'-isopropylidene)-bis (ortho methoxy)phenol (PBMP).

6. The alkoxy polycarbonate of claim 1, wherein the ortho alkoxy bisphenol monomer is at least 1 wt % derived from bio-based material.

7. The alkoxy polycarbonate of claim 6, wherein the bio-based material comprises at least one lignocellulosic material, plant material, bio-based oil, pyrolysis oil, biorefinery waste, or a combination thereof.

8. The alkoxy polycarbonate of claim 1, wherein the polycarbonate is a co-polycarbonate comprising repeating carbonate units derived from the ortho alkoxy bisphenol monomer and at least one additional phenolic monomer; and
   wherein the additional phenolic monomer does not exhibit a half maximal inhibitory concentration ($IC_{50}$) less than 0.00025M for alpha or beta in vitro estradiol receptors.

9. The alkoxy polycarbonate of claim 8, wherein the additional phenolic monomer comprises resorcinol, hydroquinone, methyl hydroquinone, t-butyl hydroquinone, di-t-butyl hydroquinones (DTBHQ), biphenols, tetramethyl bisphenol-A, spiro biindane bisphenols (SBIBP), bis-(hydroxy aryl)-N-aryl isoindolinones, hydrogenated bisphenol-A, 4,4'-(diphenylmethylene)diphenol, or a combination thereof.

10. The alkoxy polycarbonate of claim 1, wherein the polycarbonate is a co-polycarbonate comprising repeating carbonate units derived from the ortho alkoxy bisphenol monomer and at least one diol monomer or dicarboxylic acid monomer, or a combination thereof; and wherein the diol monomer or dicarboxylic acid monomer does not exhibit a half maximal inhibitory concentration ($IC_{50}$) less than 0.00025M for alpha or beta in vitro estradiol receptors.

11. The alkoxy polycarbonate of claim 10, wherein the diol monomer comprises cyclohexanedimethanol, 2,2',4,4'-tetramethyl-1,3-cyclobutanediol, isosorbide, or a combination thereof.

12. The alkoxy polycarbonate of claim 10, wherein the at least one dicarboxylic acid monomer comprises isophthalic acid, terephthalic acid, a $C_6$ to $C_{36}$ aliphatic dicarboxylic acids, furan dicarboxylic acids, naphthalene dicarboxylic acids, sebacic acid, or a combination thereof.

13. The alkoxy polycarbonate of claim 1, further comprising at least one additive comprising a stabilizer, antioxidant, colorant, impact modifier, flame retardant, anti-drip additive, mold release additive, lubricant, plasticizer, mineral additive, reinforcement additive, or a combination thereof; and wherein each of the at least one additive does not exhibit a half maximal inhibitory concentration ($IC_{50}$) less than 0.00025M for alpha or beta in vitro estradiol receptors.

14. The alkoxy polycarbonate of claim 1, further comprising at least one phosphorus compound and wherein when the polycarbonate is subjected to conditions effective to provide at least one phosphorous compound hydrolysis product, each of the at least one phosphorous compound hydrolysis product does not exhibit a half maximal inhibitory concentration ($IC_{50}$) less than 0.00025M for alpha or beta in vitro estradiol receptors.

15. The alkoxy polycarbonate of claim 14, wherein the phosphorous compound comprises a diphenyl alkyl phosphite, phenyl dialkyl phosphite, trialkyl phosphite, dialkyl phosphite, triphenyl phosphite, diphenyl pentaerythritol diphosphite, or any combination thereof.

16. The alkoxy polycarbonate of claim 14, wherein the phosphite has a Mw greater than 200 Daltons.

17. The alkoxy polycarbonate of claim 14, wherein the phosphorus compound comprises an aryl phosphate selected from the group consisting of triphenyl phosphate, resorcinol phenyl diphosphate, spirobiindane phenyl diphosphate, di-tertbutyl hydroquinone phenyl diphosphate, biphenol phenyl diphosphate, hydroquinone phenyl diphosphate, or a combination thereof.

18. The alkoxy polycarbonate of claim 1, wherein the alkoxy polycarbonate is end capped with aliphatic alcohols, phenol, phenyl chloroformate, guaiacol, ortho alkoxy phenols or a combination thereof.

19. The alkoxy polycarbonate of claim 1, wherein the alkoxy polycarbonate comprises less than about 100 ppm of bromide and less than about 100 ppm of chloride.

20. The alkoxy polycarbonate of claim 1, wherein the alkoxy polycarbonate comprises at least 20 wt % ortho alkoxy bisphenol monomer.

21. The alkoxy polycarbonate of claim 1, wherein the alkoxy polycarbonate exhibits a Tg in the range of from 120° C. to 300° C.

22. A polymer blend comprising:
a) a first polymer component comprising at least one alkoxy polycarbonate according to claim 1; and
b) a second polymer component.

23. The polymer blend of claim 22, wherein the second polymer component comprises one or more of at least one polyester, styrene acrylonitrile, acrylonitrile butadiene styrene, methyl methacrylate, methacrylate butadiene styrene, styrene maleic anhydride, styrene butadiene styrene, styrene ethylene butadiene styrene, polystyrene, polyolefin, polyetherimide, or a combination thereof.

24. An article of manufacture comprising the alkoxy polycarbonate according to claim 1.

25. The article of claim 24, wherein the article is made by a melt forming process selected from the group consisting of: injection molding, blow molding, sheet and film extrusion, profile extrusion, thermoforming, additive manufacturing, compression molding, fiber extrusion and powder sintering.

26. The article of claim 25, wherein the article has a wall thickness of from 1.0 to 5.0 mm, a percent transmission above 70% and a percent haze below 10%.

27. The article of claim 25, wherein the article is exposed to water or steam in its end use.

28. A method for preparing an alkoxy bisphenol monomer, the method comprising:
a) providing a phenol having at least one alkoxy substituent ortho to the hydroxyl group;
b) providing a ketone; and
c) reacting the phenol and ketone in the presence of an acidic catalyst under conditions effective to provide a reaction product comprising an ortho alkoxy bisphenol monomer;
wherein the ortho alkoxy bisphenol monomer does not exhibit a half maximal inhibitory concentration (IC$_{50}$) less than 0.00025M for alpha or beta in vitro estradiol receptors.

29. The method of claim 28, wherein the alkoxy bisphenol monomer is made by batch or continuous process, or combination thereof.

30. The method of claim 28, wherein the phenol having at least one alkoxy substituent ortho to the hydroxyl group comprises guaiacol (2-methoxyphenol).

31. The method of claim 28, wherein the phenol having at least one alkoxy substituent ortho to the hydroxyl group is at least 1 wt % derived from bio-based material.

32. The method of claim 28, wherein conditions effective comprise reacting the phenol and ketone in the presence of an acidic catalyst.

33. The method of claim 31, wherein the catalyst comprises H$_2$SO$_4$, an ion exchange resin catalyst, a cation acidic ion exchange resin catalyst, sulfonated polystyrene resin cross linked with divinyl benzene, trifluoro acetic acid, trifluromethane sulfonic acid, solid acid catalysts, C$_1$-C$_{24}$ alkyl or alkyl aryl sulfonic acid, HCl, or a combination thereof.

34. The method of claim 28, wherein the phenol and ketone are provided at a molar ratio of at least about 2:1.

35. The method of claim 28, wherein the ortho alkoxy bisphenol monomer has a structure represented by a formula:

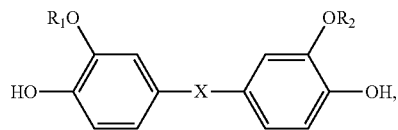

wherein each of R1 and R2 is independently selected from C$_1$-C$_{26}$ alkyl and C$_6$-C$_{26}$ alkaryl; and wherein X is a bridging group connecting the two hydroxy-substituted aromatic groups selected from —O—, —S—, —S(O)—, —S(O)$_2$—, —C(O)—, or a C$_{3-18}$ organic group; and where the bridging group and the hydroxy substituent of each C$_6$ arylene group are disposed meta, or para to each other on the C$_6$ arylene group bearing the phenolic (OH) functionality.

36. The method of claim 35, wherein each of R1 and R2 is methyl.

37. The method of claim 28, wherein the ketone comprises a C$_3$-C$_{26}$ ketone.

38. The method of claim 28, wherein the ketone is acetone.

39. The method of claim 28, wherein the reaction product comprises at least about 50 wt % of the ortho alkoxy bisphenol monomer.

40. The method of claim 28, wherein the reaction product is 4,4'(2,2'-isopropylidene)-bis(ortho methoxy)phenol (PBMP).

41. The method of claim 28, comprising:
a) providing guaiacol;
b) providing acetone, with less than 1% aldehyde impurity present; and
c) reacting the guaiacol and acetone in the presence of an acidic catalyst under conditions effective to provide a reaction product comprising 4,4'(2,2'-isopropylidene)-bis(ortho methoxy)phenol (PBMP);
wherein the PBMP does not exhibit a half maximal inhibitory concentration (IC$_{50}$) less than 0.00025M for alpha or beta in vitro estradiol receptors.

42. A method for preparing an alkoxy polycarbonate comprising:
a) providing the alkoxy bisphenol monomer of claim 28;
b) providing a carbonyl source reactant; and
c) reacting the bisphenol monomer and carbonyl source reactant in the presence of a catalyst under conditions effective to provide a polycondensation reaction product comprising an alkoxy polycarbonate;
wherein when the alkoxy polycarbonate provided in step c) is subjected to conditions effective to provide at least one hydrolysis product, each of the at least one hydrolysis products does not exhibit a half maximal inhibitory concentration (IC$_{50}$) less than 0.00025M for alpha or beta in vitro estradiol receptors; and
wherein the alkoxy polycarbonate comprises:
a) a Mw in the range of from 3,000 to 80,000 Daltons;
b) a phenolic end group content less than 20 meq/kg;
c) a total chloride content less than 20 ppm;
d) a transition metal content less than 20 ppm; and
e) a residual phenolic monomer content less than 100 ppm.

43. The method of claim 42, wherein the alkoxy bisphenol monomer is 4,4'(2,2'-isoPropylidene)-Bis(ortho Methoxy) Phenol (PBMP).

44. The method of claim 42, wherein the catalyst comprises C$_1$ to C$_6$ trialkyl amine.

45. The method of claim 42, further comprising the step of providing at least one additional monomer comprising an additional phenolic monomer, or diol monomer, or dicarboxylic acid, or phenolic carboxylic acid monomer or a combination thereof;
- wherein the additional monomer does not exhibit a half maximal inhibitory concentration ($IC_{50}$) less than 0.00025M for alpha or beta in vitro estradiol receptors; and
- wherein step c) comprises reacting the additional monomer, the bisphenol monomer, and the carbonyl source reactant in the presence of a catalyst under conditions effective to provide a polycondensation reaction product comprising a co-alkoxy polycarbonate.

46. The method of claim 45, wherein the additional phenolic monomer comprises resorcinol, hydroquinone, methyl hydroquinone, t-butyl hydroquinone, di-t-butyl hydroquinones (DTBHQ), biphenols, tetramethyl bisphenol-A, spiro biindane bisphenols (SBIBP), bis-(hydroxy aryl)-N-aryl isoindolinones, hydrogenated bisphenol-A, 4,4'-(diphenylmethylene)diphenol, or a combination thereof.

47. The method of claim of 45, wherein the diol monomer comprises cyclohexanedimethanol, 2,2',4,4'-tetramethyl-1,3-cyclobutanediol, isosorbide, or a combination thereof.

48. The method of claim 45, wherein the dicarboxylic acid monomer comprises isophthalic acid, terephthalic acid, a $C_6$ to $C_{36}$ aliphatic dicarboxylic acids, furan dicarboxylic acids, naphthalene dicarboxylic acids, sebacic acid, or a combination thereof.

* * * * *